(12) United States Patent
Crouse et al.

(10) Patent No.: US 8,394,774 B2
(45) Date of Patent: Mar. 12, 2013

(54) PESTICIDAL COMPOSITIONS

(75) Inventors: Gary D. Crouse, Noblesville, IN (US); Thomas C. Sparks, Greenfield, IN (US); CaSandra L. McLeod, Indianapolis, IN (US); Annette V. Brown, Indianapolis, IN (US); Thomas L. Siddall, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 452 days.

(21) Appl. No.: 12/703,970

(22) Filed: Feb. 11, 2010

(65) Prior Publication Data

US 2010/0204165 A1 Aug. 12, 2010

Related U.S. Application Data

(60) Provisional application No. 61/151,549, filed on Feb. 11, 2009.

(51) Int. Cl.
  *A61K 31/7034* (2006.01)
  *A61K 31/7042* (2006.01)
  *A61K 31/7048* (2006.01)
  *A61K 31/7056* (2006.01)
  *A61K 31/706* (2006.01)

(52) U.S. Cl. ............ 514/25; 514/32; 536/4.1; 536/17.4; 536/17.6; 536/17.9; 536/18.2

(58) Field of Classification Search .................. None
See application file for complete search history.

(56) References Cited

U.S. PATENT DOCUMENTS

2009/0209476 A1  8/2009  Crouse et al.

FOREIGN PATENT DOCUMENTS

WO     WO 98/047894 A1    10/1998
WO     PCT/US2009/033711    7/2009
WO     PCT/US10/023850    2/2010

OTHER PUBLICATIONS

Bertsch et al., "Surface-Active Polyhydroxy Compounds XIV. The Reaction of 4-isocyanato-trans-stilbene with Sucrose and of 4,4'-diisocyanato-trans-stilbene with alpha-D-Glucose" Journal Fur Practische Chemie (1961) vol. 13 pp. 138-140.*
Bertsch et al., "Surface-Active Polyhydroxy Compounds. XIII" Journal Fur Praktische Chemie (1961) vol. 13 pp. 134-137.*
English translation of Bertsch et al. above (1961) vol. 13 pp. 134-137.*
L. Zhou et al.: "Metabolites of an Orally Active Antimicrobial Prodrug, 2,5-Bis(4-Amidophenyl) Furan-Bis-0-Methylam Idoxime, Identified by Liquid Chromatography/Tandem Mass Spectrometry" J. Mass Spectrom., vol. 39, 2004, pp. 351-360, XP002536691 the whole document.
Yuan J J et al: "Disposition of a specific cyclooxygenase-2 inhibitor valdecoxib, in human" Drug Metabolism and Disposition, Williams and Wilkins, Baldimore, MD, US, vol. 30, No. 9, Jan. 1, 2002, pp. 1013-1021, XP002311613.

* cited by examiner

*Primary Examiner* — Eric S Olson
(74) *Attorney, Agent, or Firm* — Carl D. Corvin

(57) ABSTRACT

The invention disclosed in this document is related to the field of pesticides and their use in controlling pests. A compound having the following structure is disclosed.

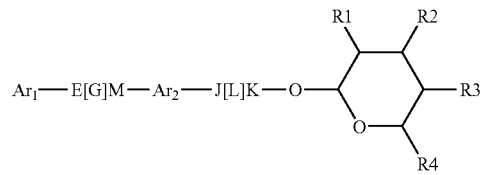

7 Claims, No Drawings

PESTICIDAL COMPOSITIONS

FIELD OF THE INVENTION

This application claims the benefit of U.S. Provisional Application Ser. No. 61/151,549 filed on 11 Feb. 2009, the entire disclosure of which is hereby incorporated by reference. The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

Substituents (Non-Exhaustive List)

The examples given for the substituents are (except for halo) non-exhaustive and must not be construed as limiting the invention disclosed in this document.

"Alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"Halo" means fluoro, chloro, bromo, and iodo.

"Haloalkoxy" means a haloalkyl further consisting of a carbon-oxygen single bond, for example, fluoromethoxy, difluoromethoxy, and trifluoromethoxy, 2-fluoroethoxy, 1,1,2,2,2-pentafluoroethoxy, 1,1,2,2-tetrafluoro-2-bromoethoxy and 1,1,2,2-tetrafluoroethoxy.

"Haloalkyl" means an alkyl further consisting of, from one to the maximum possible number of, identical or different, halos, for example, fluoromethyl, difluoromethyl, trifluoromethyl, 2-fluoroethyl, 2,2,2-trifluoroethyl, chloromethyl, trichloromethyl, and 1,1,2,2-tetrafluoroethyl.

"Halophenyloxy" means a phenyloxy having one or more, identical or different, halos.

"Hydroxyalkyl" means an alkyl having one or more hydroxy groups.

DETAILED DESCRIPTION OF THE INVENTION

The compounds of this invention have the following formula:

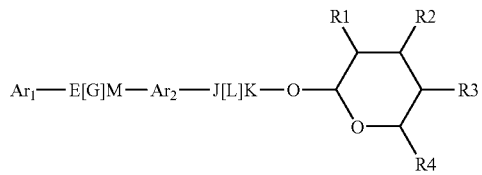

wherein:

(a) $Ar_1$ is (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $(C_1$-$C_6$ haloalkyl)$O(C_1$-$C_6$ haloalkyl)$O$, $C_1$-$C_6$(hydroxy)haloalkyl, $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl) phenyl, and phenoxy);

(b) E is N, C, or CR5;

(c) G is a double or triple bond;

(d) M is N, C, or CR5, (provided that when E is a nitrogen atom "N" then M is a nitrogen atom "N", and when E is a carbon atom "C", then M is a carbon atom "C", and when E is "CR5" then M is "CR5";

(c) $Ar_2$ is (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $(C_1$-$C_6$ haloalkyl)$O(C_1$-$C_6$ haloalkyl)O, $C_1$-$C_6$ (hydroxy)(halo)alkyl, $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl) phenyl, and phenoxy);

(d) J is O, N, NR5, CR5, or C=O;

(e) L is a single or double bond;

(f) K is CR5, C=O, N, NR5, or C=S;

(g) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

(h) R2 is H, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

(i) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

(j) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, $(C_1$-$C_6$ alkyl)$O(C_1$-$C_6$ alkyl);

(k) R5 is (each independently) H, $C_1$-$C_6$ alkyl, $C_1$-$C_6$ haloalkyl, $C_3$-$C_6$ cycloalkyl, or $C_3$-$C_6$ halocycloalkyl; and (l) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy.

In another embodiment of this invention:

$Ar_1$ is substituted phenyl, wherein said substituted phenyl, has one or more substituents independently selected from $C_1$-$C_6$ haloalkyl, $C_1$-$C_6$ alkoxy, $C_1$-$C_6$ haloalkoxy, $C(=O)$ $(C_1$-$C_6$ alkyl), $(C_1$-$C_6$ haloalkyl)$O(C_1$-$C_6$ haloalkyl)O, and $C_1$-$C_6$ (hydroxy)haloalkyl.

In another embodiment of this invention:

$Ar_1$ is substituted phenyl, wherein said substituted phenyl, has one or more substituents independently selected from $C_1$-$C_6$ haloalkyl, $C_1$-$C_6$ alkoxy, $C_1$-$C_6$ haloalkoxy, and $(C_1$-$C_6$ haloalkyl)$O(C_1$-$C_6$ haloalkyl)O.

In another embodiment of this invention: $Ar_e$ is phenyl.

In another embodiment of this invention: J is N, NR5, or CR5.

In another embodiment of this invention: K is C=O, or N.

In another embodiment of this invention: R1, R2, and R3, are (each independently) a $C_1$-$C_6$ alkoxy.

In another embodiment of this invention: R4 is a $C_1$-$C_6$ alkyl.

In another embodiment of this invention: R5 is H.

While these embodiments have been expressed, other embodiments and combinations of these expressed embodiments and other embodiments, are possible.

Preparation of Pyranose-Intermediates

A wide variety of pyranoses (in different structural forms, for example, D- and L-) can be used to make the compounds of this invention. For example, the following non-exhaustive list of pyranoses may be used: ribose, arabinose, xylose, lyxose, ribulose, xylulose, allose, altrose, glucose, mannose, gulose, idose, galactose, talose, psicose, fructose, sorbose, tagatose, fucose, mycarose, quinovose, oleandrose, rhamnose, and paratose. In most of the examples below, L-rhamnose was used to make pyranose-intermediates.

In general, pyranose-intermediates can be made as follows (using L-rhamnose as an example). O-Alkylated rhamnose derivatives can be prepared from commercially available L-rhamnose or L-rhamnose hydrate by using an alkyl iodide and powdered potassium hydroxide KOH) in dry dimethyl sulfoxide (DMSO) at from 5° C. to 15° C. The fully alkylated product is then isolated by extraction of the DMSO solution with hexanes, followed by concentration of the hexane layer under vacuum. This intermediate alkyl pyranoside is then treated directly with aqueous hydrochloric acid (HCl) or other aqueous acid, which forms the free hydroxy sugar, usually as a mixture of α and β anomers.

Alternatively, the per-alkylated L-rhamnose can be isolated by hydrolysis of spinosad or other tri-(O-alkyl)rhamnosylated natural product, using conditions similar to those described for the isolation of methyl oleandroside from avermectin $B_2$ (Loewe et al. *J. Org. Chem.* 1994, 59, 7870). Thus, treatment of technical spinosad with excess concentrated sulfuric acid in dry methyl alcohol (MeOH) results in hydrolysis of the rhamnose sugar and conversion into the methyl pyranoside. The pure methyl pyranoside can then be removed from the reaction medium by exhaustive extraction with hexanes or other hydrocarbon solvent. The pure rhamnopyranoside can then be isolated in ca. 65-75% overall yield by distillation of the crude liquor under vacuum.

The 3-O-ethyl-2,4-di-O-methyl rhamnose can be prepared in a similar manner, starting from spinetoram. Other alkylated derivatives can be likewise produced by starting with the appropriately functionalized spinosoid derivatives, which are made from any spinosyn factor which has one or more free hydroxyl groups attached to rhamnose (for example, spinosyn J) using conditions described in DeAmicis et al. U.S. Pat. No. 6,001,981, 1999.

Reaction of the methyl pyranoside of L-rhamnose with one equivalent of phenylboronic acid, under conditions that allow for removal of water, results in the formation of a boron acetal. Treatment of this acetal with an alkyl iodide and silver oxide, in a polar aprotic solvent such as N,N-dimethylformamide (DMF), at from 0° C. to 110° C. results in a selective alkylation at C3-OH, giving the 3-O-alkyl methyl pyranoside. This material can then be further methylated at positions 2-OH and 4-OH with methyl iodide, using conditions described previously. The fully alkylated rhamnose can then be hydrolyzed as described above to give 2,4-di-O-methyl-3-O-alkyl L-rhamnose.

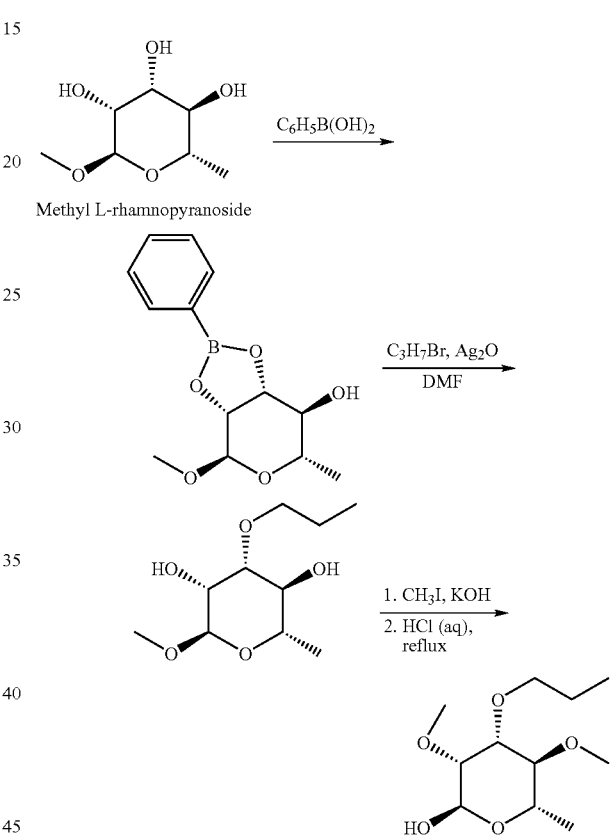

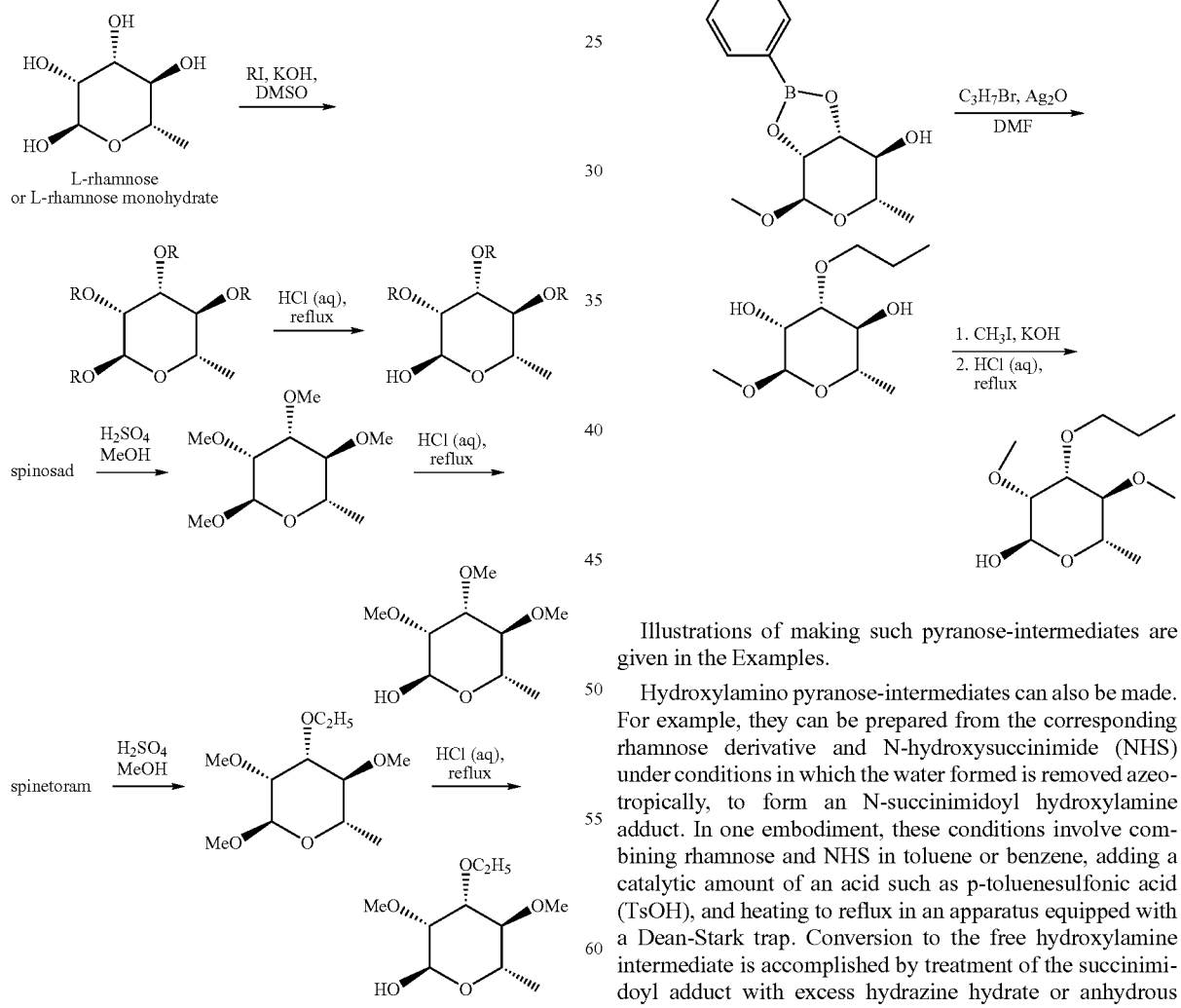

Illustrations of making such pyranose-intermediates are given in the Examples.

Hydroxylamino pyranose-intermediates can also be made. For example, they can be prepared from the corresponding rhamnose derivative and N-hydroxysuccinimide (NHS) under conditions in which the water formed is removed azeotropically, to form an N-succinimidoyl hydroxylamine adduct. In one embodiment, these conditions involve combining rhamnose and NHS in toluene or benzene, adding a catalytic amount of an acid such as p-toluenesulfonic acid (TsOH), and heating to reflux in an apparatus equipped with a Dean-Stark trap. Conversion to the free hydroxylamine intermediate is accomplished by treatment of the succinimidoyl adduct with excess hydrazine hydrate or anhydrous hydrazine in an alcoholic solvent such as MeOH or ethyl alcohol (EtOH). Reaction of the O-rhamnosyl hydroxylamine with an aldehyde or ketone using EtOH or other lower alcohol solvent at from ambient temperature to reflux then produces an O-rhamnosyl oxime.

A rhamnose precursor that is selectively alkylated with a larger substituent at C3 has been described (see, for example, Pozsgay et al. *Can. J. Chem.* 1987, 65, 2764). An alternate route, which avoids the use of tin reagents, is described below.

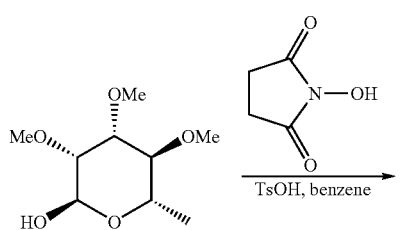

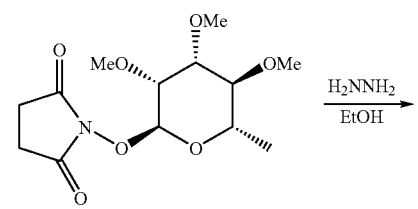

Preparation of Diaryl-Intermediates

Compounds of this invention are prepared by linking the above-described pyranoses to a diaryl intermediate, Ar1-E[G]M-Ar2, by means of a covalent linker J[L]KQ (defined above). A wide variety of diaryl precursors can be used to prepare compounds of this invention, provided that they contain a suitable functional group on Ar2 to which the pyranose intermediate can be attached in order to form the covalent linker. Suitable functional groups include an amino, oxoalkyl, formyl, or carboxylic acid group. These intermediates can be prepared by methods previously described in the chemical literature. Several of these methods follow.

Preparation of Oxime-Linked Compounds

Oxime linked compounds can be prepared from the corresponding aryl aldehydes or ketones by reaction with the corresponding 2-hydroxylamino sugar, in an organic solvent such as MeOH or EtOH, at temperatures between 0 and 100° C.

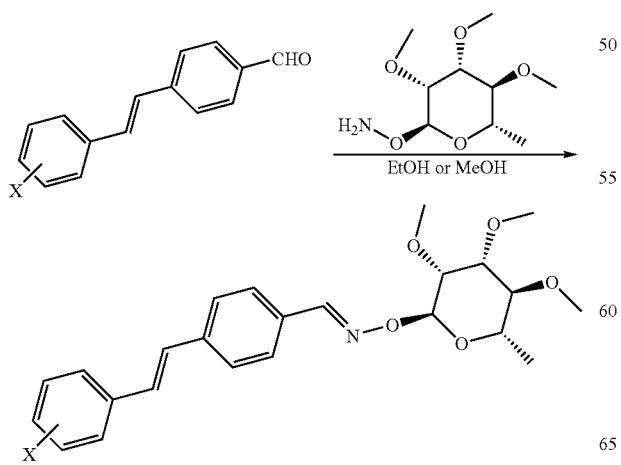

Preparation of Carbamate-Linked Compounds

Carbamate or thio-carbamate linked compounds can be prepared from the corresponding aryl amines by conversion into either an isocyanate, isothiocyanate or p-nitrophenyl carbamate, followed by treatment with the appropriate —ROH and an organic or inorganic base in a suitable solvent such as tetrahydrofuran (THF), at temperatures between 0 and 100° C.:

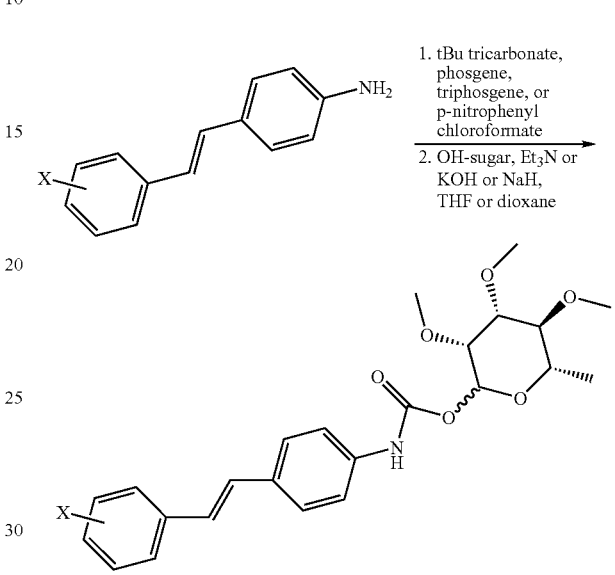

In these reactions, the α-configuration at C1 of the rhamnose moiety is usually the major product, although a minor amount of the β-anomer is also formed. These two isomers may be separated chromatographically, or they may be used as a mixture.

Preparation of compounds within the scope of this invention can be done by the synthesis of an appropriate intermediate containing an acid, aldehyde, ketone, or amino functional group for attachment to the pyranose-intermediate.

EXAMPLES

These examples are for illustration purposes and are not to be construed as limiting the invention disclosed in this document to only the embodiments disclosed.

Example 1

Preparation of (3R,4R,5S,6S)-2,3,4,5-tetramethoxy-6-methyl-tetrahydropyran (Compound E-1)

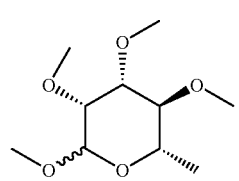

A solution of L-rhamnose hydrate (40 grams (g), 0.22 mole (mol)) in dry dimethyl sulfoxide (DMSO; 450 milliliters (mL)) was placed in a 2-liter (L) 3-neck round bottom flask and stirred mechanically while powdered potassium hydroxide (KOH; 75 g, 1.34 mol) was added in one portion. Iodomethane (187 g, 1.32 mol) was added to this solution at a rate such that the temperature of the solution was maintained below 30° C. A dry ice-acetone bath was used intermittently to maintain this temperature. After the addition was complete (about 2 hours (h)), the solution was stirred an additional 3 h, then it was allowed to stand at ambient temperature overnight. This clear solution was then extracted with hexanes (4×500 mL), and the combined hexane solution was washed with brine before drying and evaporation of solvent to provide a light orange solution (44 g, 92%). Distillation gave 40 g of a colorless oil, by 150° C. (0.5 mm Hg).

Example 2

Preparation of (3R,4R,5S,6S)-3,4,5-trimethoxy-6-methyl-tetrahydro-pyran-2-ol (Compound E-2)

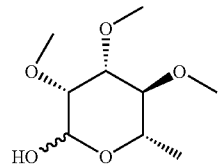

A solution of E-1 (35.7 g, 0.162 mol) in 2 N hydrochloric acid (HCl; 300 mL) was heated at 98° C. for 5 h, was then cooled to room temperature, and was extracted with dichloromethane (CH$_2$Cl$_2$; 4×170-mL). The combined extracts were dried over magnesium sulfate (MgSO$_4$) and decolorized with charcoal. Concentration gave the title compound (24.7 g, 74%) as a viscous oil. A portion of the crude product (960 milligrams (mg)) was vacuum distilled using a Kuhgelrohr apparatus collecting 890 mg at 145-155° C. (1-2 mm).

Example 3

Preparation of (3R,4R,5S,6S)-4-ethoxy-2,3,5-trimethoxy-6-methyl-tetrahydropyran (Compound E-3)

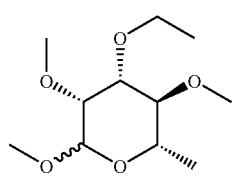

Sulfuric acid (H$_2$SO$_4$, 98%; 300 mL, 5.6 mol) was added slowly to a stirred solution of methyl alcohol (2.5 liters (L)) in a 4-L Erlenmeyer flask. When the solution had cooled to ambient temperature, 3'-OEt spinosyn J/L (350 g, 0.47 mol) (prepared as in DeAmicis et al., U.S. Pat. No. 6,001,981, 1999) was added and the resulting solution was heated at reflux for 6 h. The cooled solution was transferred to a 4-L separatory funnel and extracted with hexanes (3×1 L). The combined organic solution was dried and concentrated in vacuo, then distilled using a Kugelrohr to provide a colorless oil (65 g, 60%), by 165° C. (10 mTorr).

Example 4

Preparation of (2R,3R,4R,5R,6S)-2,3,5-trimethoxy-6-methyl-4-propoxy-tetrahydropyran (Compound E-5)

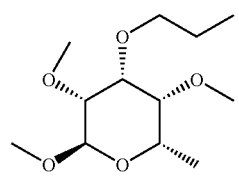 [SMILES: CCCO[C@H]1[C@@H](OC)[C@H](OC)O[C@@H](C)[C@H]1OC]

Step 1. (2R,3R,4R,5R,6S)-2-Methoxy-6-methyl-4-propoxy-tetrahydropyran-3,5-diol. Following the procedure described by Oshima et al. (*Tetrahedron Lett.* 1997, 38, 5001) for preparation of the 3,4-boronate ester of methyl α-L-fucopyranoside, methyl α-L-rhamnopyranoside was converted into the 2,3-boronate ester. The crude ester (10.0 g, 37.7 millimoles (mmol)) was dissolved in toluene (150 mL) and treated with iodopropane (8.0 g, 47 mmol), silver oxide (21.8 g, 94.3 mmol) and triethylamine (4.77 g, 47.1 mmol). The solution was heated to 100° C. and allowed to stir overnight (16 h). After cooling and filtering, the solution was concentrated to a gummy oil and was purified by silica gel chromatography eluting with an ethyl acetate (EtOAc)-hexane gradient to obtain 5.9 g of pure product.

Step 2. The material from Step 1 was methylated using MeI and KOH, under conditions described in Example 1 to furnish compound E-5

The pyranose-intermediates listed in Table 1 were prepared by the routes described earlier and illustrated in Examples 1-4.

An example of the preparation of 2-O-succinimidoyl pyranose-intermediates is described below.

Example 5

Preparation of 1-((2S,3R,4R,5S,6S)-3,4,5-trimethoxy-6-methyl-tetrahydropyran-2-yloxy)-pyrrolidine-2,5-dione (Compound E-23)

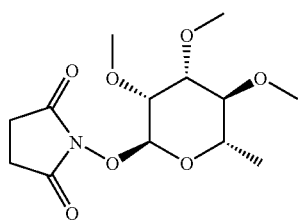 [SMILES: CO[C@@H]1[C@@H](OC)[C@H](C)O[C@@H](ON2C(=O)CCC2=O)[C@@H]1OC]

To a stirred solution of 2,3,4-tri-O-methyl-L-rhamnose (6.5 g, 31.5 mmol) and N-hydroxysuccinimide (5.4 g, 47 mmol) in benzene (50 mL) was added p-toluenesulfonic acid (50 mg, cat.). The solution was heated to reflux and water (H$_2$O) was collected using a Dean-Stark trap. After 4 h, the solution was cooled and the supernatant toluene layer was separated from a small amount of insoluble gum. The organic layer was washed with a saturated solution of sodium bicarbonate (NaHCO$_3$; 20 mL), then dried over MgSO$_4$ and concentrated to a solid. Recrystallization from ether (Et$_2$O)-hexanes gave the title compound (4.95 g, 52%) as an off-white solid.

Example 6

Preparation of 1-((2S,3R,4R,5S,6S)-5-hydroxy-3,4-dimethoxy-6-methyl-tetrahydropyran-2-yloxy)-pyrrolidine-2,5-dione (Compound E-24)

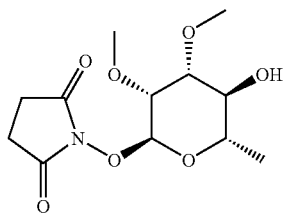 [SMILES: CO[C@@H]1[C@@H](O)[C@H](C)O[C@@H](ON2C(=O)CCC2=O)[C@@H]1OC]

A solution of (2R,3R,4R,5S,6S)-5-benzyloxy-3,4-dimethoxy-6-methyl-tetrahydropyran-2-ol (prepared according to Wu et al., *Carbohydr. Res.* 1998, 306, 493; 10.5 g, 26.6 mmol), N-hydroxysuccinimide (5.0 g, 50 mmol) and TsOH (250 mg, cat.) in benzene (100 mL) was heated at reflux for 24 h with removal of H$_2$O using a Dean-Stark trap. The brown solution was cooled, filtered, washed with saturated NaHCO$_3$ solution and concentrated. The gummy oil was purified by silica gel chromatography, eluting with 70:30 hexanes-acetone. The pure O-succinimide (7.5 g, 14.5 mmol) was then transferred to a 500-mL Parr hydrogenation apparatus and debenzylated using Pd(OH)$_2$/C (0.95 g) in EtOH (75 mL). The solution, which took up 19 pounds per square inch (psi) of hydrogen over 24 h, was then filtered and concentrated, leaving a solid residue which was recrystallized from EtOH to give a white solid (3.25 g).

The O-succinimidyl pyranose-intermediates listed in Table 2 were prepared by the routes described earlier and illustrated in Examples 5 and 6.

An example of the preparation of 2-hydroxylamino pyranose-intermediates from the corresponding O-succinimidoyl pyranose-intermediates is described next.

Example 7

Preparation of O-((2S,3R,4R,5S,6S)-3,4,5-trimethoxy-6-methyl-tetrahydropyran-2-yl)-hydroxylamine (Compound E-30)

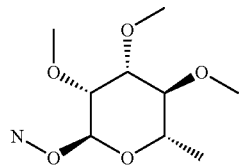

The 2,3,4-tri-O-methyl-N-succinimidyl rhamnose derivative E-23 (0.50 g, 1.65 mmol), prepared according to Example 5, was dissolved in absolute EtOH (5 mL) and treated with an excess of hydrazine hydrate (0.4 g, 8 mmol). The solution was allowed to stir at ambient temperature for 60 minutes (min), whereupon a voluminous white precipitate formed. Additional EtOH (5 mL) was added, and the solution was stirred at ambient temperature overnight. The solution was filtered and concentrated, then purified by chromatography (100% EtOAc) to furnish 265 mg (74% yield) of the hydroxylamine as a crystalline solid.

The pyranose-intermediates in Table 3 were prepared by the routes described earlier and as illustrated in Example 7.

Example 8

Preparation of 4-[(E)-2-(4-trifluoromethoxyphenyl)-vinyl]-benzaldehyde O-((2S,3R,4R,5S,6S)-3,5-dimethoxy-6-methyl-4-propoxy-tetrahydropyran-2-yl)-oxime (Compound 1)

Step 1. 4-[(E)-2-(4-Trifluoromethoxyphenyl)-vinyl]-benzonitrile. To a round bottom flask flushed with nitrogen was added potassium phosphate, tribasic (617 mg, 2.9 mmol) in dimethyl acetamide (DMA; 2 mL), 4-trifluoromethoxy bromobenzene (500 mg, 2.1 mmol) and 4-cyanovinylbenzene (322 mg, 2.5 mmol), followed by palladium acetate (23 mg, 5 mol %). The solution was heated to 140° C. with stirring for 12 h. The solution was then allowed to cool to room temperature, poured into H$_2$O, extracted with EtOAc, and washed with brine. The combined organic layers were dried over MgSO$_4$, filtered and concentrated. The crude material was purified by column chromatography (EtOAc in hexanes, 0-75%) to furnish a yellow solid (543 mg, 90%) that was pure by gas chromatography/mass spectral (GC-MS) analysis. This material was used directly in next reaction without further purification.

Step 2. 4-[(E)-2-(4-Trifluoromethoxyphenyl)-vinyl]-benzaldehyde. The cyano diphenyl styrene (543 mg, 1.88 mmol) was dissolved in dry CH$_2$Cl$_2$ (10 mL) and cooled to −78° C. in a dry ice/acetone bath. To this solution was added dropwise diisobutylaluminum hydride in hexanes (3.7 mL, 3.7 mmol). The reaction was allowed to stir 4 h while warming to room temperature. The desired aldehyde was formed exclusively by GC-MS. Water and methanol were added to the reaction mixture, which caused bubbling and gel formation. The heterogeneous mixture was diluted with CH$_2$Cl$_2$ and filtered through a Biotage phase separator frit. The organic layer was collected and concentrated to give a yellow solid (450 mg, 81%) that was pure product by GC-MS. The product was used directly in the next reaction without further purification.

Step 3. 4-[(E)-2-(4-Trifluoromethoxyphenyl)-vinyl]-benzaldehyde O-((2S,3R,4R,5S,6S)-3,5-dimethoxy-6-methyl-4-propoxy-tetrahydropyran-2-yl)-oxime. The aldehyde prepared in Step 1 (0.1 g, 0.3 mmol) and Compound E-32 (0.3 mmol) were dissolved in absolute EtOH (10 mL) and the solution was heated to 40° C. with stirring overnight. Water (5 mL) was then added to the cooled solution which caused a white precipitate to form. The solution was partitioned between H$_2$O (5 mL) and EtOAc (3×5 mL), and the combined organic layers were dried over MgSO$_4$, filtered and concentrated to give a dark yellow solid. Purification by normal phase column chromatography (EtOAc-hexanes gradient) gave the desired product (72 mg, 40%) as a light yellow solid:

mp 124-132° C.; $^1$H NMR (300 MHz, CDCl$_3$) δ 8.13 (s, 1H), 7.63 (d, J=9.0 Hz, 2H), 7.54 (m, 4H), 7.21 (d, J=9.0 Hz, 2H), 7.11 (d, J=9.0 Hz, 2H), 5.63 (s, 1H), 3.71 (m 1H), 3.70-3.50 (m, 4H), 3.59 (s, 3H), 3.55 (s, 3H), 3.20 (t, J=9.0 Hz, 1H), 1.68 (m, 2H), 1.31 (d, J=6.0 Hz, 3H), 0.98 (t, J=7.6 Hz, 3H); ESIMS m/z 524 ([M+H]$^+$).

The following compounds were prepared using conditions outlined in Example 8.

4-[(E)-2-(4-Trifluoromethylphenyl)-vinyl]-benzaldehyde O-((2S,3R,4R,5S,6S)-4-ethoxy-3,5-dimethoxy-6-methyl-tetrahydropyran-2-yl)-oxime (Compound 2)

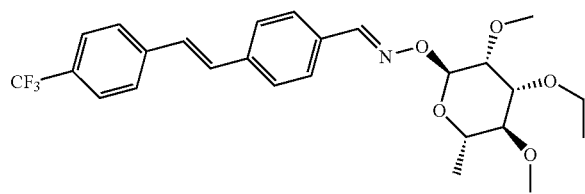 [SMILES: CCO[C@@H]1[C@@H](OC)[C@H](C)O[C@@H](O/N=C/c2ccc(/C=C/c3ccc(C(F)(F)F)cc3)cc2)[C@@H]1OC]

Oxime formation yielded 60% of a tan solid: mp 150-153° C.; $^1$H NMR (400 MHz, DMSO-d$_6$) δ 8.41 (s, 1H), 7.84 (d, J=8.1 Hz, 2H), 7.75-7.67 (m, 6H), 7.46 (s, 2H), 5.49 (d, J=2.0 Hz, 1H), 3.73-3.66 (br s, 2H), 3.56-3.47 (m, 3H), 3.45 (s, 3H), 3.43 (s, 3H), 3.04 (t, J=10.0 Hz, 1H), 1.17 (m, 6H); ESIMS m/z 494 ([M+H]$^+$).

4-{(E)-2-[4-(1,1,2,2-Tetrafluoro-2-heptafluoropropyloxy-ethyl)-phenyl]-vinyl}-benzaldehyde O-(2S,3R,4R,5S,6S)-4-ethoxy-3,5-dimethoxy-6-methyl-tetrahydropyran-2-yl)-oxime (Compound 3)

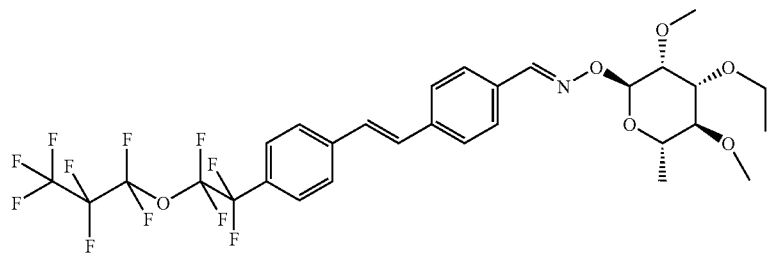 [SMILES: CCO[C@@H]1[C@@H](OC)[C@H](C)O[C@@H](O/N=C/c2ccc(/C=C/c3ccc(C(F)(F)C(F)(F)OC(F)(F)C(F)(F)C(F)(F)F)cc3)cc2)[C@@H]1OC]

Oxime formation yielded 84% of a light yellow oil: $^1$H NMR (400 MHz, DMSO-d$_6$) δ 8.40 (s, 1H), 7.68 (m, 4H), 7.50 (m, 3H), 7.40 (d, J=4.0 Hz, 1H), 7.15 (d, J=8.0 Hz, 1H), 5.48 (s, 1H), 3.74 (m, 1H), 3.67 (m, 1H), 3.55-3.46 (m, 4H), 3.45 (s, 3H), 3.43 (s, 3H), 3.04 (t, J=9.2 Hz, 1H), 1.17 (m, 6H); ESIMS m/z 707 ([M−H]$^−$).

4-[(E)-2-(4-Acetyl-phenyl)-vinyl]-benzaldehyde O-((2S,3R,4R,5S,6S)-4-ethoxy-3,5-dimethoxy-6-methyl-tetrahydropyran-2-yl)-oxime (Compound 4)

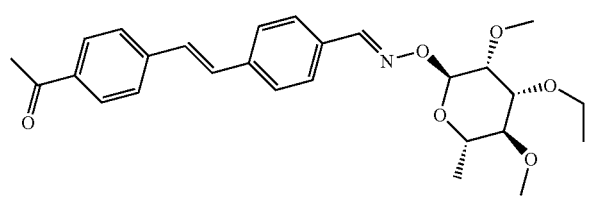 [SMILES: CCO[C@@H]1[C@@H](OC)[C@H](C)O[C@@H](O/N=C/c2ccc(/C=C/c3ccc(C(C)=O)cc3)cc2)[C@@H]1OC]

Oxime formation yielded 56% of a tan solid: mp 164-167° C.; $^1$H NMR (400 MHz, DMSO-d$_6$) δ 8.41 (s, 1H), 7.97 (d, J=8.0 Hz, 2H), 7.77 (d, J=8.0 Hz, 2H), 7.72 (d, J=8.0 Hz, 2H), 7.68 (d, J=8.3 Hz, 2H), 7.45 (s, 2H), 5.48 (s, 1H), 3.86 (s, 3H), 3.74 (br s, 1H), 3.73-3.66 (m, 1H), 3.54-3.46 (m, 3H), 3.45 (s, 3H), 3.43 (s, 3H), 3.04 (t, J=8.0 Hz, 1H), 1.17 (m, 6H); ESIMS m/z 485 ([M+H$_2$O]$^+$).

4-[(E)-2-(4-Trifluoromethoxyphenyl)-vinyl]-benzaldehyde O-((2S,3R,4R,5S,6S)-4-ethoxy-3,5-dimethoxy-6-methyl-tetrahydropyran-2-yl)-oxime (Compound 5)

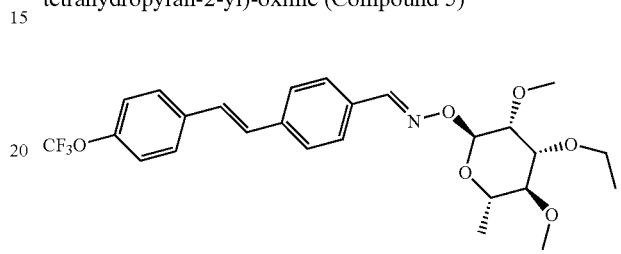

Oxime formation yielded 24% of a light yellow solid: mp 91-101° C.; $^1$H NMR (300 MHz, CDCl$_3$) δ 8.13 (s, 1H), 7.63 (d, J=9.0 Hz, 2H), 7.55-7.51 (m, 3H), 7.23-7.17 (m, 3H), 7.11 (d, J=9.0 Hz, 2H), 5.64 (d, J=3.0 Hz, 1H), 3.79-3.60 (m, 5H), 3.59 (s, 3H), 3.55 (s, 3H), 3.20 (t, J=9.0 Hz, 1H), 1.32-1.24 (m, 6H); ESIMS m/z 532 ([M+Na]$^+$).

4-[(E)-2-(3-Trifluoromethylphenyl)-vinyl]-benzaldehyde O-((2S,3R,4R,5S,6S)-4-ethoxy-3,5-dimethoxy-6-methyl-tetrahydropyran-2-yl)-oxime (Compound 6)

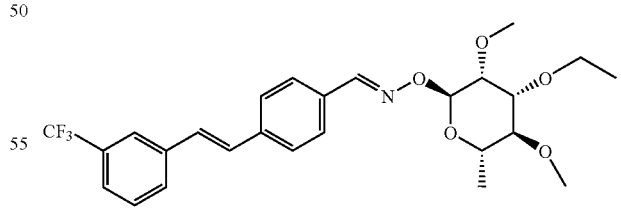

Oxime formation yielded 62% of a brown oil: $^1$H NMR (400 MHz, DMSO-d$_6$) δ 8.40 (s, 1H), 7.99 (s, 1H), 7.94 (br s, 1H), 7.72-7.63 (m, 6H), 7.47 (s, 2H), 5.48 (s, 1H), 3.74 (m, 1H), 3.73-3.68 (m, 1H), 3.54-3.47 (m, 3H), 3.45 (s, 3H), 3.43 (s, 3H), 3.04 (t, J=8.0 Hz, 1H), 1.17 (m, 6H); ESIMS m/z 494 ([M+H]$^+$).

4-[(E)-2-(4-Pentafluoroethyloxyphenyl)-vinyl]-benzaldehyde O-((2S,3R,4R,5S,6S)-4-ethoxy-3,5-dimethoxy-6-methyl-tetrahydropyran-2-yl)-oxime (Compound 7)

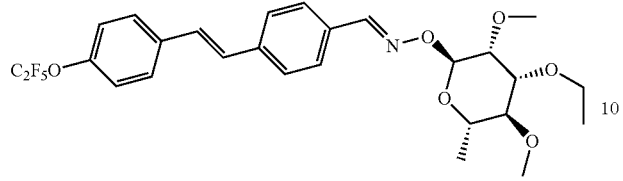

Oxime formation yielded 7 mg (6%) of a light yellow glass: $^1$H NMR (300 MHz, CDCl$_3$) δ 8.13 (s, 1H), 7.63 (d, J=8.1 Hz, 2H), 7.56-7.51 (m, 5H), 7.24 (d, J=4.5 Hz, 2H), 7.11 (d, J=8.1 Hz, 2H), 5.63 (d, J=1.8 Hz, 1H), 3.79-3.60 (m, 5H), 3.59 (s, 3H), 3.55 (s, 3H), 1.32-1.25 (m, 6H); ESIMS m/z 582 ([M+H]$^+$).

4-[(E)-2-(4-Trifluoromethyloxyphenyl)-vinyl]-benzaldehyde O-(2S,3R,4R,5S,6S)-3,4,5-trimethoxy-6-methyl-tetrahydropyran-2-yl)-oxime (Compound 8)

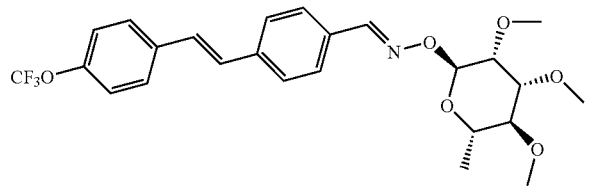

Oxime formation yielded 37 mg (30%) of a white solid: mp 120-128° C.; $^1$H NMR (400 MHz, CDCl$_3$) δ 8.40 (s, 1H), 7.75 (d, J=8.0 Hz, 2H), 7.68-7.65 (m, 4H), 7.42-7.30 (m, 4H), 5.50 (s, 1H), 3.80-3.79 (m, 1H), 3.56-3.52 (m, 1H), 3.43 (s, 3H), 3.42 (s, 3H), 3.40-3.37 (m, 1H), 3.38 (s, 3H), 3.05 (t, J=8.0 Hz, 1H), 1.17 (d, J=4.0 Hz, 3H); ESIMS m/z 496 ([M+H]$^+$).

4-[(E)-2-(3-Trifluoromethylphenyl)-vinyl]-benzaldehyde O-((2S,3R,4R,5S,6S)-3,4,5-trimethoxy-6-methyl-tetrahydropyran-2-yl)-oxime (Compound 9)

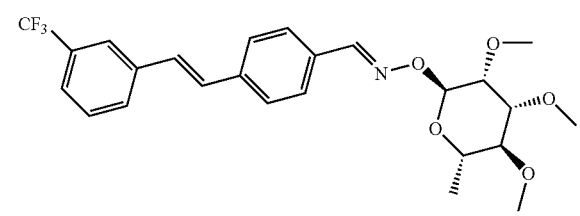 [SMILES: CO[C@@H]1[C@@H](OC)[C@H](C)O[C@@H](O/N=C/c2ccc(/C=C/c3cccc(C(F)(F)F)c3)cc2)[C@@H]1OC]

The material (65 mg, 50%) was isolated as a clear glass: $^1$H NMR (400 MHz, DMSO-d$_6$) δ 8.40 (s, 1H), 7.98 (s, 1H), 7.72 (br s, 1H), 7.70 (dd, J=12.0, 8.0 Hz, 4H), 7.64 (br s, 2H), 7.48 (s, 2H), 5.51 (br s, 1H), 3.56-3.43 (m, 3H), 3.43 (s, 3H), 3.42 (s, 3H), 3.38 (s, 3H), 3.05 (t, J=8.0 Hz, 1H), 1.17 (d, J=4.0 Hz, 3H); ESIMS m/z 480 ([M+H]$^+$).

4-[(E)-2-(4-Trifluoromethylphenyl)-vinyl]-benzaldehyde O-((2S,3R,4R,5S,6S)-4-propoxy-3,5-dimethoxy-6-methyl-tetrahydropyran-2-yl)-oxime (Compound 10)

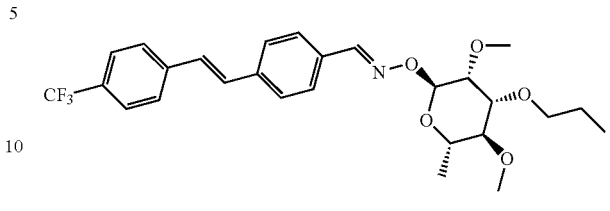

The material (210 mg, 77%) was isolated as a colorless solid: mp 163-166; $^1$H NMR (300 MHz, CDCl$_3$) δ 8.16 (s, 1H), 7.66 (d, J=8 Hz, 2H), 7.63 (s, 4H), 7.56 (d, J=8 Hz, 2H), 7.2 (s, 2H), 5.66 (s, 1H), 3.73-3.57 (m, 10H), 3.23 (t, J=9 Hz, 1H), 1.71 (m, 2H), 1.33 (d, J=6 Hz, 2H), 1.0 (t, J=7.5 Hz, 3H).

4-{(E)-2-[4-(2,2,2-Trifluoro-1-hydroxy-1-trifluoromethyl-ethyl)-phenyl]-vinyl}-benzaldehyde O-((2S,3R,4R,5S,6S)-4-ethoxy-3,5-dimethoxy-6-methyl-tetrahydropyran-2-yl)-oxime (Compound 11)

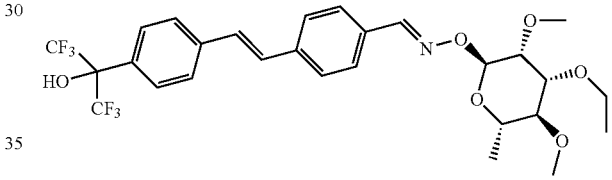

The material (250 mg, 86%) was isolated as a yellow gum: $^1$H NMR (300 MHz, CDCl$_3$) δ 8.16 (s, 1H), 7.74 (d, J=8 Hz, 2H), 7.65-7.45 (m, 6H), 7.15 (s, 2H), 5.62 (d, J=1.4 Hz, 1H), 4.67 (s, 1H), 4.8-4.5 (m, 11H), 3.22 (t, J=8 Hz, 1H), 1.35-1.2 (m, 6H); ESIMS m/z 614 ([M+Na]$^+$).

4-[(E)-2-(4-Trifluoromethylphenyl)-vinyl]-benzaldehyde O-((2S,3R,4R,5S,6S)-3,4,5-trimethoxy-6-methyl-tetrahydropyran-2-yl)-oxime (Compound 12)

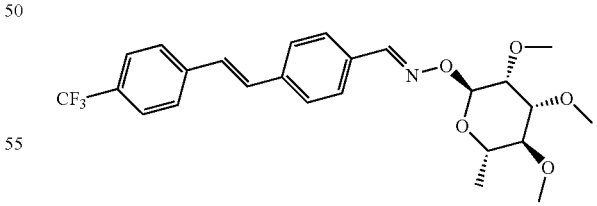

The material (95 mg, 56%) was isolated as a white solid: mp 147-151° C.; $^1$H NMR (400 MHz, DMSO-d$_6$) δ 8.42 (s, 1H), 7.85 (d, J=8.0 Hz, 2H), 7.76-7.67 (m, 6H), 7.47 (s, 2H), 5.52 (d, J=4.0 Hz, 1H), 3.80 (t, J=4.0 Hz, 1H), 3.56-3.51 (m, 1H), 3.43 (s, 3H), 3.42 (s, 3H), 3.41-3.39 (m, 1H), 3.38 (s, 3H), 3.04 (t, J=8.0 Hz, 1H), 1.17 (d, J=4.0 Hz, 3H).

Example 9

General Procedure for Alkyne Coupling to Bromobenzene

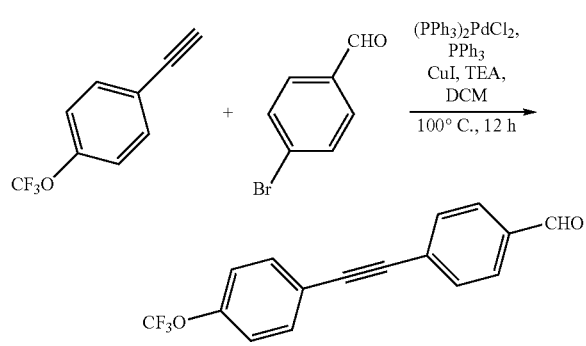

The alkyne (0.5 g, 2.7 mmol), bromobenzaldehyde (0.45 g, 2.4 mmol), Pd catalyst (0.04 g, 0.06 mmol), CuI (0.02 g, 0.12 mmol), triphenyl phosphine (0.03 g, 0.12 mmol) and triethylamine (3.5 mL) were combined in 1.5 mL of anhydrous DMF. The solution was heated to 100° C. with stirring under a nitrogen atmosphere for a total of 12 h. The solution was then cooled to room temperature, filtered through Celite, and concentrated to a brown solid which was purified by normal phase column chromatography (EtOAc in hexanes) to give the diarylated acetylene (512 mg, 65%), which was used directly without further characterization.

Example 10

Preparation of 4-(4-trifluoromethoxyphenylethynyl)-benzaldehyde O-((2S,3R,4R,5S,6S)-4-ethoxy-3,5-dimethoxy-6-methyl-tetrahydropyran-2-yl)-oxime (Compound 13)

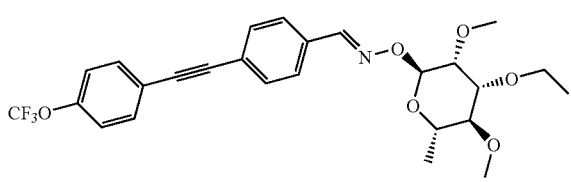

The aldehyde (0.12 g, 0.42 mmol) in EtOH (10 mL) was treated with hydroxylamine intermediate E-31 (0.10 g, 0.42 mmol) and the solution was heated to 50° C. with stirring. When the reaction was completed (by LC-MS analysis), the solution was cooled to room temperature, diluted with $H_2O$ and extracted with EtOAc (3×10 mL). The combined organic layers were dried over $MgSO_4$, filtered and concentrated to give a yellow solid that was purified by normal phase column chromatography (EtOAc in hexanes). The desired product (120 mg, 56%) was isolated as a sticky yellow solid: mp 82-87° C.; $^1$H NMR (300 MHz, $CDCl_3$) δ 8.13 (s, 1H), 7.63 (d, J=9.0 Hz, 2H), 7.55 (m, 4H), 7.21 (d, J=9.0 Hz, 2H), 5.63 (s, 1H), 3.75-3.60 (m, 5H), 3.59 (s, 3H), 3.55 (s, 3H), 3.19 (t, J=9.0 Hz, 1H), 1.32-1.27 (m, 6H); ESIMS m/z 509 ([M+H]$^+$).

The following compounds were prepared using conditions outlined in Examples 9 and 10.

4-(4-Trifluoromethylphenylethynyl)-benzaldehyde O-((2S,3R,4R,5S,6S)-4-ethoxy-3,5-dimethoxy-6-methyl-tetrahydropyran-2-yl)-oxime (Compound 14)

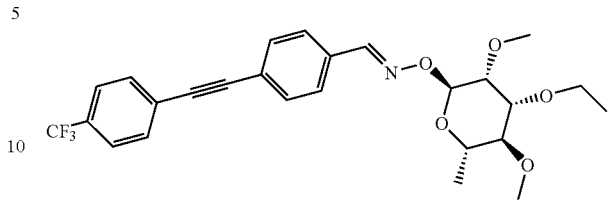

The product was isolated as an off-white solid (137 mg, 76%): mp 130-132° C.; $^1$H NMR (400 MHz, DMSO-$d_6$) δ 8.46 (s, 1H), 7.81 (s, 4H), 7.73 (d, J=8 Hz, 2H), 7.70 (d, J=8 Hz, 2H), 5.49 (s, 1H), 3.75 (br s, 1H), 3.52 (m, 1H), 3.51-3.46 (m, 3H), 3.45 (s, 3H), 3.43 (s, 3H), 3.04 (t, J=8.0 Hz, 1H), 1.19-1.15 (m, 6H); ESIMS m/z 492 ([M+H]$^+$).

4-(4-Trifluoromethylphenylethynyl)-benzaldehyde O-((3R,4R,5S,6S)-3,4,5-trimethoxy-6-methyl-tetrahydropyran-2-yl)-oxime (Compound 15)

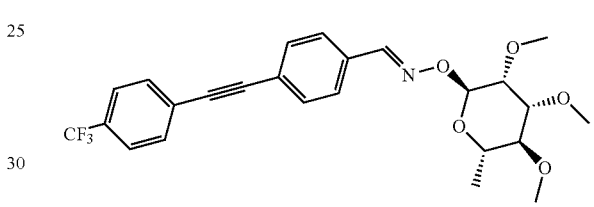

The product (78 mg, 84%) was isolated as a white solid: mp 128-136° C.; $^1$H NMR (400 MHz, $CDCl_3$) δ 8.14 (s, 1H), 7.65-7.63 (m, 6H), 7.56 (d, J=8.0 Hz, 2H), 5.65 (s, 1H), 3.76-3.75 (m, 1H), 3.68-3.64 (m, 1H), 3.58 (s, 3H), 3.55 (s, 3H), 3.54 (s, 3H), 3.51-3.49 (m, 1H), 3.20 (t, J=8.0 Hz, 1H), 1.32 (d, J=4.0 Hz, 3H); ESIMS m/z 500 ([M+Na]$^+$).

Example 11

Preparation of {4-[(E)-2-(4-trifluoromethylphenyl)-vinyl]-phenyl}-carbamic acid (2S,3R,4R,5S,6S)-4-ethoxy-3,5-dimethoxy-6-methyl-tetrahydropyran-2-yl ester (Compound 16)

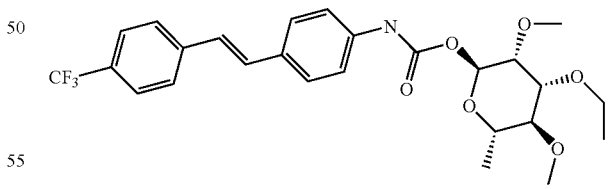

To a solution of 4-(4-trifluoromethylphenylvinyl)phenyl amine (25 mg, 0.095 mmol) in dry THF (4 mL) was added 4-nitrophenyl chloroformate (19 mg, 0.095 mmol). The solution was allowed to stir under nitrogen for 1 h, and then the rhamnopyranose (Compound E-8; 20 mg, 0.95 mmol) was added, followed by powdered KOH (25 mg, 0.4 mmol). The solution was allowed to stir at ambient temperature for 4 h, and then it was diluted with $Et_2O$ (25 mL), washed with $H_2O$, dried with $MgSO_4$ and concentrated. The crude red oil was purified by silica gel chromatography to give Compound 16:

¹H NMR (300 MHz, CDCl₃) δ 7.61 (s, 4H), 7.52 (d, J=8 Hz, 2H), 7.47 (d, J=8 Hz, 2H), 7.2 (d, J=15 Hz, 1H), 7.05 (d, J=15 Hz, 1H), 6.74 (s, 1H), 6.2 (d, J=1.5 Hz, 1H), 3.8-3.5 (m, 11H), 3.23 (t, J=8.0 Hz, 1H), 1.33-1.25 (m, 6H); ESIMS m/z 531 ([M+Na]⁺).

The following compounds were prepared using the conditions described in Example 11.

{4-[(E)-2-(4-Ethoxyphenyl)-vinyl]-phenyl}-carbamic acid (2S,3R,4R,5S,6S)-3,4,5-tri-methoxy-6-methyl-tetrahydropyran-2-yl ester (Compound 17)

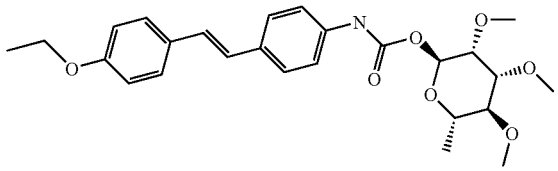 [SMILES: CCOc1ccc(/C=C/c2ccc(NC(=O)O[C@@H]3O[C@@H](C)[C@H](OC)[C@@H](OC)[C@H]3OC)cc2)cc1]

The material (68 mg, 40%) was isolated as a yellow foam: ¹H NMR (300 MHz, CDCl₃) δ 7.38-7.22 (m, 8H), 6.84 (d, J=8.24 Hz, 2H), 6.64 (s, 1H), 5.65 (s, 1H), 4.06 (q, J=7.24 Hz, 2H), 3.76-3.75 (m, 1H), 3.68-3.64 (m, 1H), 3.58 (s, 3H), 3.55 (s, 3H), 3.54 (s, 3H), 3.51-3.49 (m, 1H), 3.20 (t, J=8.0 Hz, 1H), 1.38-1.28 (m, 6H); ESI m/z 485 ([M]⁺).

{4-[(E)-2-(4-Pentafluoroethyloxyphenyl)-vinyl]-phenyl}-carbamic acid (2S,3R,4R,5S,6S)-4-propoxy-3,5-dimethoxy-6-methyl-tetrahydropyran-2-yl ester (Compound 18)

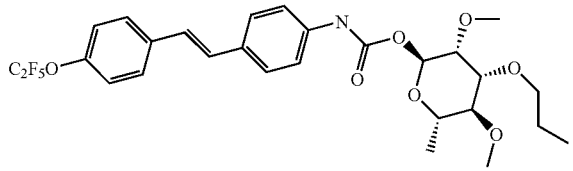

The material (18 mg, 12%) was isolated as a gummy solid: ¹H NMR (300 MHz, CDCl₃) δ 7.5-7.45 (m, 6H), 7.21 (d, J=8.4 Hz, 2H), 7.05 (s, 2H), 6.91 (s, 1H), 5.27 (br s, 1H), 3.8 (m, 1H), 3.69-3.50 (m, 10H), 3.23 (t, J=8 Hz, 1H), 1.69 (m, 2H), 1.3 (d, J=6 Hz, 3H), 0.98 (t, J=7.5 Hz, 3H); ESIMS m/z 591 ([M+H]⁺).

Example 12

Preparation of [4-(3-trifluoromethoxyphenylazo)-phenyl]-carbamic acid (2S,3R,4R,5S,6S)-3,5-dimethoxy-4-ethoxy-6-methyl-tetrahydropyran-2-yl ester (Compound 19)

Step 1. 4-(3-Trifluoromethoxyphenylazo)aniline. 3-Trifluoromethoxyaniline (2.0 g, 11 mmol) was dissolved in CH₂Cl₂ (20 mL), and treated with a mixture of Oxone™ (11 g, 18 mmol) in H₂O (20 mL), and the solution was stirred for 20 h at 25° C. The organic phase was separated and the aqueous phase was extracted with CH₂Cl₂ (2×20 mL), the combined organic phases were dried (Na₂SO₄) and evaporated. The crude nitroso compound was dissolved in acetic acid (40 mL), treated with p-phenylenediamine (2.0 g, 19 mmol), and allowed to stir for 60 h. The volatiles were removed under vacuum and the residue was purified by silica gel chromatography with 0 to 20% EtOAc/hexane to give the azo aniline (900 mg, 27%) as an orange oil: ¹H NMR (300 MHz, CDCl₃) δ 7.77-7.84 (m, 3H), 7.71 (s, 1H), 7.46-7.52 (m, 1H), 7.22-7.26 (m, 1H), 6.71-6.75 (m, 2H), 4.12 (br s, 2H); ESIMS m/z 282 ([M+H]⁺).

Step 2. Compound 19. 4-(3-Trifluoromethoxyphenylazo) aniline (200 mg, 0.71 mmol) was dissolved in anhydrous THF (5 mL), treated with 4-nitrophenyl chloroformate (170 mg, 0.82 mmol) and stirred for 1 h at 25° C. (3R,4R,5S,6S)-4-Ethoxy-3,5-dimethoxy-6-methyl-tetrahydropyran-2-ol (175 mg, 0.78 mmol) and 95% sodium hydride (NaH; 35 mg, 2.1 mmol) were added, and the mixture was stirred for 2 h. H₂O (20 µL, 1 mmol) was added and stirring was continued for 1 h. The mixture was diluted with H₂O (10 mL) and EtOAc (15 mL). The separated organic phase was washed with H₂O (5 mL) and brine (5 mL), was dried (Na₂SO₄) and was concentrated. The residue was purified by silica gel chromatography with 0 to 30% EtOAc/hexane to give the title compound (220 mg, 59%) as an oil: ¹H NMR (400 MHz, CDCl₃) δ 7.87-7.97 (m, 3H), 7.77 (s, 1H), 7.54-7.57 (m, 4H), 6.94 (s, 1H), 6.22 (s, 1H), 3.56-3.78 (m, 11H), 3.24 (t, J=9.2 Hz, 1H), 1.28-1.36 (m, 6H); ESIMS m/z 528 ([M+H]⁺).

The following compounds were prepared using the conditions described in Example 12.

[4-(4-Trifluoromethoxy-phenylazo)-phenyl]-carbamic acid (2S,3R,4R,5S,6S)-4-ethoxy-3,5-dimethoxy-6-methyl-tetrahydropyran-2-yl ester (Compound 20)

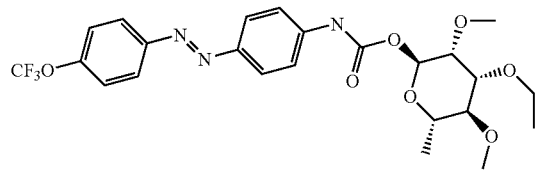

Step 1. 4-(4-Trifluoromethyoxyphenylazo)aniline. ¹H NMR (300 MHz, CDCl₃) δ 7.79-7.83 (m, 4H), 7.25-7.33 (m, 2H), 6.72-6.75 (m, 2H), 4.09 (br s, 2H); ESIMS m/z 282 (M+H).

Step 2. Compound 20. mp 158-159° C.; ¹H NMR (400 MHz, CDCl₃) δ 7.95-7.92 (m, 4H), 7.59-7.57 (d, J=8.6 Hz, 2H), 7.34 (d, J=8.1 Hz, 2H), 6.86 (s, 1H), 6.21 (s, 1H), 3.8-3.5 (m, 11H), 3.22 (t, J=9.4 Hz, 1H), 1.35-1.25 (m, 6H); ESIMS m/z 528 ([M+H]⁺).

[4-(4-Trifluoromethylphenylazo)-phenyl]-carbamic acid (2S,3R,4R,5S,6S)-4-ethoxy-3,5-dimethoxy-6-methyl-tetrahydropyran-2-yl ester (Compound 21)

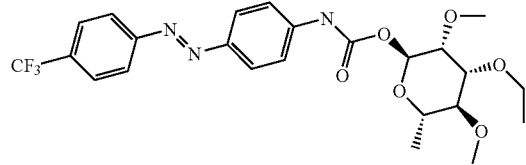 [SMILES: CCO[C@@H]1[C@@H](OC)[C@H](C)O[C@@H](OC(=O)Nc2ccc(/N=N/c3ccc(C(F)(F)F)cc3)cc2)[C@@H]1OC]

Step 1. 4-(4-Trifluoromethylphenylazo)aniline ¹H NMR (300 MHz, CDCl₃) δ 7.81-7.91 (m, 4H), 7.72 (d, J=8.2 Hz, 2H), 6.71-6.75 (m, 2H), 4.12 (br s, 2H); ESIMS m/z 266 ([M+H]⁺).

Step 2. Compound 21. mp 186-188° C.; ¹H NMR (400 MHz, CDCl₃) δ 7.89-8.2 (m, 4H), 7.77 (d, J=8.3 Hz, 2H), 7.60 (d, J=8.6 Hz, 2H), 6.91 (s, 1H), 6.21 (s, 1H), 3.77-3.57 (m, 11H), 3.22 (t, J=9.4 Hz, 1H), 1.34-1.28 (m, 6H); ESIMS m/z 512 ([M+H]⁺).

[4-(4-Pentafluoroethyloxyphenylazo)-phenyl]-carbamic acid (2S,3R,4R,5S,6S)-4-ethoxy-3,5-dimethoxy-6-methyl-tetrahydropyran-2-yl ester (Compound 22)

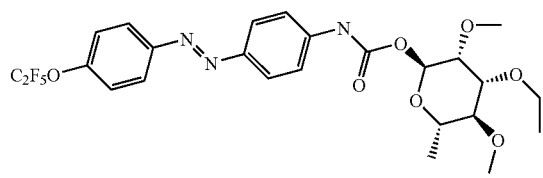

Step 1. 4-(4-Pentafluoroethoxyphenylazo)aniline ¹H NMR (300 MHz, CDCl₃) δ7.89-7.79 (m, 4H), 7.32 (d, J=8.5 Hz, 2H), 6.73-6.76 (m, 2H), 4.09 (br s, 2H); ESIMS m/z 332 ([M+H]⁺).

Step 2. Compound 22. ¹H NMR (300 MHz, CDCl₃) δ 7.96-7.92 (m, 4H), 7.60-7.57 (m, 2H), 7.38-7.35 (m, 2H), 6.86 (s, 1H), 6.26 (s, 1H), 3.75-3.45 (m, 11H), 3.22 (t, J=9.3 Hz, 1H), 1.33-1.26 (m, 6H); ESIMS m/z 578 ([M+H]⁺).

Testing Of Compounds

Bioassays on beet armyworm (BAW; *Spodoptera exigua*: Lepidoptera) were conducted using either a 96-well microtiter plate-based high throughput (HTS) bioassay or a 128-well diet tray assay. The HTS assay is based on a modification of Lewer et al. *J. Nat. Prod.* 2006, 69, 1506. BAW eggs were placed on top of artificial diet (100 μL) in each well of a 96-well microtiter plate. The diet was pretreated with test compounds (12 μg dissolved in 30 μL of DMSO-acetone-H₂O mixture) layered on top of the diet using a liquid handling system and then allowed to dry for several hours. Infested plates were then covered with a layer of sterile cotton batting and the plate lid, and then held in the dark at 29° C. Mortality was recorded at 6 days post-treatment. Each plate had six replicates. The percent mortality was calculated from the average of the six replicates. In the case of the 128-well diet assay, three to five second instar BAW larvae were placed in each well (3 mL) of the diet tray that had been previously filled with 1 mL of artificial diet to which 50 ug/cm² of the test compound (dissolved in 50 μL of 90:10 acetone-water mixture) had been applied (to each of eight wells) and then allowed to dry. Trays were covered with a clear self-adhesive cover, and held at 25° C., 14:10 light-dark for six days. Percent mortality was recorded for the larvae in each well; activity in the eight wells was then averaged. The results are indicated in Table 4. In Table 4, under both the BAW HTS and BAW 50 headings, an "A" means that the compound was tested and at least 50 percent mortality was observed whereas, "B" means that either (1) the compound was tested and less than 50 percent mortality was observed or (2) the compound was not tested.

TABLE-1

General Formula

| # | A | R1 | R2 | R3 | R4 | Sugar | M.S. | bp | ¹H NMR (CDCl₃, δ) |
|---|---|----|----|----|----|-------|------|-----|---------------------|
| E-1 | OCH₃ | OCH₃ | OCH₃ | OCH₃ | CH₃ | L-rhamnose | | 150° C. (0.5 mm Hg) | 5.28 (m, 1H), 3.85 (m, 1H), 3.66 (m, 1H), 3.60-3.50 (m, 1H), 3.58 (s, 3H), 3.53 (s, 6H), 3.37 (s, 3H), 3.16 (t, 1H), 1.31 (d, J = 6.2 Hz, 3H) |
| E-2 | OH | OCH₃ | OCH₃ | OCH₃ | CH₃ | L-rhamnose | | 145-155° C. (1 mm Hg) | 5.28 (s, 1H), 3.83 (m, 1H), 3.7-3.45 (m, 11H), 3.16 (t, J = 9.2 Hz, 1H), 3.0 (s, 1H), 1.31 (d, J = 6 Hz, 3H) |
| E-3 | OCH₃ | OCH₃ | OC₂H₅ | OCH₃ | CH₃ | L-rhamnose | 202.9 (M − MeOH) | 165° C. (10 m Torr) | 4.71 (d, J = 1.8 Hz, 1H), 3.77-3.50 (m, 11H), 3.37 (s, 3H), 3.13 (t, J = 9.4 Hz, 1H), 1.32 (d, J = 6.3 Hz, 3H), 1.27 (t, J = 7.0 Hz, 3H) |
| E-4 | OC₂H₅ | OC₂H₅ | OC₂H₅ | OC₂H₅ | CH₃ | L-rhamnose | 299.1 (M + Na) | 180° C. (10 m Torr) | 4.72 (d, J = 1.8 Hz) and 4.30 (s, total 1H), 4.0-3.35 (series of m, 10H), 3.2 (m, 2H), 1.3-1.1 (m, 15H) |
| E-5 | OCH₃ | OCH₃ | OC₃H₇ | OCH₃ | CH₃ | L-rhamnose | | 175° C. (10 m Torr) | 4.70 (d, J = 1.8 Hz, 1H), 3.77-3.50 (m, 11H), 3.37 (s, 3H), 3.13 (t, J = 9.4 Hz, 1H), 1.62 (m, 2H), 1.32 (d, J = 6.3 Hz, 3H), 0.98 (t, J = 7.5 Hz, 3H) |
| E-6 | OCH₃ | OCH₃ | O-allyl | OCH₃ | CH₃ | L-rhamnose | | 175° C. (10 m Torr) | 5.98 (m, 1H), 5.32 (d, 1H), 5.20 (d, 1H), 4.50 (s, 1H), 4.18 (d, 2H), 3.62-3.50 (m, 9H), 3.28 (s, 3H), 3.17 (t, J = 6.3 Hz, 1H), 1.33 (d, J = 6.3 Hz, 3H) |

TABLE-1-continued

General Formula

| # | A | R1 | R2 | R3 | R4 | Sugar | M.S. | bp | $^1$H NMR (CDCl$_3$, δ) |
|---|---|----|----|----|----|-------|------|-----|---------------------|
| E-7 | OCH$_3$ | OCH$_3$ | OC$_4$H$_9$ | OCH$_3$ | CH$_3$ | L-rhamnose | | 165° C. (5 m Torr) | 4.71 (s, 1H), 3.62-3.50 (m, 11H), 3.35 (s, 3H), 3.17 (t, 1H), 1.6 (m, 2H), 1.4 (m, 2H), 1.33 (d, J = 6.3 Hz, 3H), 0.98 (t, J = 7.5 Hz, 3H) |
| E-8 | OH | OCH$_3$ | OC$_2$H$_5$ | OCH$_3$ | CH$_3$ | L-rhamnose | 202.9 | 165° C. (9 m Torr) | 5.35 (m, J = 3.2, 2.0 Hz, 1H), 3.84-3.62 (m, 5H), 3.59 (s, 3H), 3.53 (s, 3H), 3.16 (t, J = 9.5 Hz, 1H), 2.73 (d, J = 3.4 Hz, 1H), 1.33-1.26 (m, 6H) |
| E-9 | OH | OC$_2$H$_5$ | OC$_2$H$_5$ | OC$_2$H$_5$ | CH$_3$ | L-rhamnose | 248.2 (M+) | 203° C. (5 m Torr) | 5.2 (s) and 4.65 (dd, J = 1.2, 9 Hz, anomeric proton signals, total 1H, ratio 64:36 α:β); 4.10-3.45 (m, 8H), 3.36-3.20 (m, 2H), 1.37-1.13 (m, 12H) |
| E-10 | OH | OCH$_3$ | OC$_3$H$_7$ | OCH$_3$ | CH$_3$ | L-rhamnose | 220.2 (M +) | 185° C. (5 m Torr) | 5.25 (dd, J = 3.2, 2.0 Hz) and 4.61 (m, total 1H), 3.80 (m, 1H), 3.70-3.50 (m, 9H), 3.36-3.05 (m, 1H), 1.60 (m, 2H), 1.30 (m, 5H), 0.95 (t, J = 7.5 Hz, 3H) |
| E-11 | OH | OCH$_3$ | O-allyl | OCH$_3$ | CH$_3$ | L-rhamnose | 254.9 (M + Na) | 175° C. (10 m Torr) | 5.95 (m, 1H), 5.3 (m, 1H), 5.19 (m, 1H), 5.21 and 4.61 (both m, α and β anomers, total 1H), 4.20 (m, 2H), 3.80 (m, 1H), 3.70-3.50 (m, 7H), 3.40-3.10 (m, 3H), 1.3 (m, 3H) |
| E-12 | OH | OCH$_3$ | OC$_4$H$_9$ | OCH$_3$ | CH$_3$ | L-rhamnose | 248.2 (M+) | 189° C. (5 m Torr) | 5.35 (dd, J = 3.2, 2.0 Hz) and 4.45 (m, total 1H), 3.80 (m, 1H), 3.70-3.50 (m, 10H), 3.36-3.05 (m, 1H), 2.73 (d, J = 3.4 Hz, 1H), 1.60 (m, 2H), 1.40 (m, 2H), 1.33 (d, J = 6 Hz, 3H), 0.95 (t, J = 7.5 Hz, 3H) |
| E-13 | —OH | —OCH$_3$ | —OCH$_3$ | —OCH$_3$ | CH$_2$O—CH$_3$ | L-mannose | | | 5.32 (s, 1H), 3.9 (m, 1H), 3.66-3.53 (series of m, 4H), 3.52 (s, 3H), 3.51 (s, 3H), 3.49 (s, 3H), 3.40 (s, 3H), 3.35 (m, 1H), 3.18 (d, J = 3 Hz, 1H) |
| E-14 | —OH | —OCH$_3$ | —OCH$_3$ | —OCH$_3$ | CH$_2$O—CH$_3$ | D-glucose | | | 5.33 (d, J = 3.6 Hz) and 4.60 (d, J = 4 Hz, α and β anomers, total 1H), 3.9 (m, 1H), 3.6-3.3 (series of s and m, 14H), 3.28 (m, 3H), 1.7 (s, 1H) |
| E-15 | —OCH$_3$ | —OCH$_3$ | —OCH$_3$ | —OCH$_3$ | —H$_2$ | L-xylose | 207 (M + H) | | 4.77 (d, J = 3.5 Hz) and 4.15 (d, J = 7.4 Hz, total 1H in a 0.27:1 α:β ratio), 4.00 (dd, J = 11.6, 5.0 Hz, 1H), 4.03-2.93 (series of s and m, 16H) |
| E-16 | —OH | —OCH$_3$ | —OCH$_3$ | —OCH$_3$ | —H$_2$ | L-xylose | 175 (M − H$_2$O) | | 5.23 (t, J = 3.4 Hz) and 4.60 (t, J = 6.3 Hz, total 1H in a 1.5:1 α:β ratio), 4.01-2.97 (series of s and m, 15H) |
| E-17 | —OCH$_3$ | —OCH$_3$ | —OCH$_3$ | —OCH$_3$ | —H$_2$ | L-lyxose | 207 (M + H) | | 4.69 (d, J = 3.0 Hz, 1H, α anomer), 3.77 (dd, J = 10.8, 4.7 Hz, 1H), 3.62-3.32 (series of s and m, 16H) |
| E-18 | —OH | —OCH$_3$ | —OCH$_3$ | —OCH$_3$ | —H$_2$ | L-lyxose | 175 (M − H$_2$O) | | 5.18-5.11 (m, 1H, mixture of α and β anomers), 4.84 (d, J = 10.1 Hz, 0.4 H), 3.98-3.37 (series of s and m, 14H), 3.11 (d, J = 4.2 Hz, 0.6H) |
| E-19 | —OCH$_3$ | —OCH$_3$ | —OCH$_3$ | —OCH$_3$ | CH$_2$O—CH$_3$ | L-glucose | 205 (M − CH$_2$OCH$_3$) | | (600 MHz, CDCl$_3$) 4.83 (d, J = 4.1 Hz) and 4.14 (d, J = 7.8 Hz, total 1H in a 0.2:1 α:β ratio), 3.66-3.36 (series of s and m, 18H), 3.29-3.26 (m, 1H), 3.17-3.13 (m, 1H), 3.01-2.94 (m, 1H) |

TABLE-1-continued

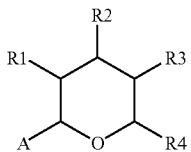

General Formula

| # | A | R1 | R2 | R3 | R4 | Sugar | M.S. | bp | ¹H NMR (CDCl₃, δ) |
|---|---|---|---|---|---|---|---|---|---|
| E-20 | —OH | —OCH₃ | —OCH₃ | —OCH₃ | CH₂O—CH₃ | L-glucose | 191 (M − CH₂OCH₃) | mp 63-67° C. | 5.33 (d, J = 3.7 Hz) and 4.58 (d, J = 7.9 Hz, total 1H in a 2.5:1 α:β ratio), 3.92-3.86 (m, 0.8H), 3.65-3.08 (series of s and m, 18H), 2.96 (dd, J = 8.8, 7.8 Hz, 0.2H) |
| E-21 | —OCH₃ | —H₂ | —OCH₃ | —OCH₃ | CH₂O—CH₃ | 2-deoxy-D-glucose | 220 (M⁺) | | 4.81 (dd, J = 3.6, 1.1 Hz) and 4.34 (dd, J = 9.5, 1.9 Hz, total 1H in a 0.29:1 α:β ratio), 3.71-3.23 (m, 16H), 3.18-3.05 (m, 1H), 2.33-2.16 (m, 1H), 1.60-1.41 (m, 1H) |
| E-22 | —OCH₃ | —H₂ | —OCH₃ | OH | CH₃ | L-oleandrose | | | 4.78 (d, J = 3.3 Hz, 1H), 3.52 (m, 1H), 3.47 (m, 1H), 3.45 (s, 3H), 3.30 (s, 3H), 3.19 (m, 1H), 2.67 (br s, 1H), 2.29 (dd, J = 4.8, 12.9 Hz, 1H), 1.51 (m, 1H), 1.32 (d, J = 6.3 Hz, 3H) |

TABLE-2

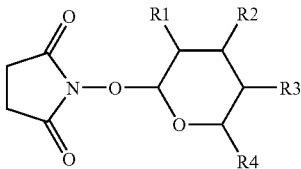

| # | R1 | R2 | R3 | R4 | Sugar | M.S. | mp | ¹H NMR (CDCl₃, δ) |
|---|---|---|---|---|---|---|---|---|
| E-23 | OCH₃ | OCH₃ | OCH₃ | CH₃ | L-rhamnose | 326.1 [M + Na]⁺ | 135° C. | 5.35 (d, J = 2.0 Hz, 1H), 4.29 (m, 1 H), 3.89 (dd, J = 3.3, 2.1 Hz, 1H), 3.55 (s, 3H), 3.54 (s, 3H), 3.52 (s, 3H), 3.51 (m, 1H), 3.18 (t, J = 9.3 Hz, 1H), 2.74 (s, 4H), 1.27 (d, J = 6.1 Hz, 3H) |
| E-24 | OCH₃ | OCH₃ | OH | CH₃ | L-rhamnose | 288 [M − H] | 163-166° C. | 5.42 (s, 1H), 4.40 (m, 1H), 4.0 (m, 1H), 3.63 (d, J = 8 Hz, 1H), 3.55-3.45 (m, 7H), 2.78 (s, 4H), 2.2 (br s, 1H), 1.30 (d, J = 6.3 Hz, 3H) |
| E-25 | OCH₃ | OC₂H₅ | OCH₃ | CH₃ | L-rhamnose | | | 5.35 (m, 1H), 4.29 (m, 1H), 3.85 (m, 1H), 3.78-3.50 (m, 9H), 3.19 (t, J = 9.5 Hz, 1H), 2.75 (s, 4H), 1.33-1.26 (m, 6H) |
| E-26 | OCH₃ | OC₃H₇ | OCH₃ | CH₃ | L-rhamnose | 354 [M + Na]⁺ | 69-71° C. | 5.35 (s, 1H), 4.29 (m, 1H), 3.84 (m, 1H), 3.78-3.50 (m, 9H), 3.19 (t, J = 9.5 Hz, 1H), 2.75 (s, 4H), 1.64 (m, 2H), 1.25 (d, J = 6.1 Hz, 3H), 0.95 (t, J = 7.5 Hz, 3H) |
| E-27 | OCH₃ | OC₄H₉ | OCH₃ | CH₃ | L-rhamnose | | | 5.32 (d, J = 1.8 Hz, 1H), 4.29 (m, 1H), 3.84 (m, 1H), 3.6-3.45 (m, 9H), 3.17 (t, J = 9.3 Hz, 1H), 2.73 (s, 4H), 1.6 (m, 2H), 1.4 (m, 2H), 1.26 (d, J = 5.7 Hz, 3H), 0.93 (t, J = 7.5 Hz, 3H) |
| E-28 | OCH₃ | OCH₃ | OCH₃ | CH₂OCH₃ | D-glucose | | | 5.52 (d, J = 4 Hz, 1H), 4.45 (d, J = 10 Hz, 1H), 3.68-3.47 (m, 12H), 3.4-3.27, (series of m, 5H), 2.72 (s, 4H) |
| E-29 | OCH₃ | OCH₃ | OCH₃ | CH₂OCH₃ | L-mannose | | | 5.44 (s, 1H), 4.29 (m, 1H), 3.90 (m, 1H), 3.7-3.55 (m, 3H), 3.54 (s, 3H), 3.53 (s, 3H), 3.52 (s, 3H), 3.53 (m, 1H), 3.38 (s, 3H), 2.73 (s, 4H) |

TABLE-3

[Structure: pyranose ring with H$_2$N-O- at anomeric position, R1, R2, R3 substituents on ring, and R4 at other anomeric position]

| # | R1 | R2 | R3 | R4 | Sugar | M.S. | Mp | $^1$H NMR (CDCl$_3$, δ) |
|---|----|----|----|----|-------|------|----|----|
| E-30 | OCH$_3$ | OCH$_3$ | OCH$_3$ | CH$_3$ | L-rhamnose | 221.7 (M + H)$^+$ | 55° C. | 5.51 (s, 2H), 4.98 (d, J = 1.8 Hz, 1H), 3.60 (m, 2H), 3.55 (s, 3H), 3.50 (s, 3H), 3.48 (s, 3H), 3.35 (dd, J = 9.2, 3.3 Hz, 1H), 3.13 (t, J = 9.4 Hz, 1H), 1.34 (dd, J = 6.2 Hz, 3H) |
| E-31 | OCH$_3$ | OC$_2$H$_5$ | OCH$_3$ | CH$_3$ | L-rhamnose | 258.1 (M + Na)$^+$ | 88° C. | 5.51 (s, 2H), 4.98 (d, J = 1.8 Hz, 1H), 3.60 (m, 4H), 3.55 (s, 3H), 3.48 (s, 3H), 3.35 (dd, J = 9.2, 3.3 Hz, 1H), 3.13 (t, J = 9.4 Hz, 1H), 1.34-1.26 (m, 6H) |
| E-32 | OCH$_3$ | OC$_3$H$_7$ | OCH$_3$ | CH$_3$ | L-rhamnose | 249.1 (M + H)$^+$ | 49° C. | 5.6 (s, 2H), 4.95 (d, J = 1.8 Hz, 1H), 3.6-3.3 (m, 11H), 3.13 (t, J = 9.3 Hz, 1H), 1.65 (m, 2H), 1.34 (d, J = 6.2 Hz, 3H), 0.97 (t, J = 7.5 Hz, 3H) |
| E-33 | OCH$_3$ | OC$_4$H$_9$ | OCH$_3$ | CH$_3$ | L-rhamnose |  | 40-42° C. | 5.6 (s, 2H), 4.97 (d, J = 1.8 Hz, 1H), 3.6-3.3 (m, 11H), 3.13 (t, J = 9.3 Hz, 1H), 1.62 (m, 2H), 1.40 (m, 2H), 1.34 (d, J = 6.2 Hz, 3H), 0.94 (t, J = 7.5 Hz, 3H) |
| E-34 | OC$_2$H$_5$ | OC$_2$H$_5$ | OC$_2$H$_5$ | CH$_3$ | L-rhamnose | 264.1 (M + Na)$^+$ | Oil | 5.5 (s, 2H), 4.90 (s, 1H), 3.9 (m, 1H), 3.80-3.50 (m, 7H), 3.4 (m, 1H), 3.25 (t, J = 9 Hz, 1H), 1.35 (d, J = 6.3 Hz, 3H), 1.27 (m, 9H) |
| E-35 | OCH$_3$ | OCH$_3$ | OH | CH$_3$ | L-rhamnose | 268 (M + AcOH) | Oil | 5.6 (br s, 2H), 4.96 (s, 1H), 3.7-3.5 (m, 3H), 3.48 (s, 3H), 3.42 (s, 3H), 3.25 (dd, J = 10.3 Hz, 1H), 2.75 (br s, 1H), 1.7 (d, J = 7 Hz, 3H) |
| E-36 | OCH$_3$ | OCH$_3$ | OCH$_3$ | CH$_2$OCH$_3$ | L-mannose | 251.1 (M + H$^+$) | 58° C. | 5.5 (br s, 2H), 5.04 (d, J = 2 Hz, 1H), 3.65-3.58 (m, 4H), 3.52 (s, 3H), 3.48 (two s, 6H), 3.42 (s, 3H), 3.45-3.39 (m, 2H) |
| E-37 | OCH$_3$ | OCH$_3$ | OCH$_3$ | CH$_3$ | L-fucose |  | 91° C. | 5.58 (s, 2H), 5.1 (d, J = 4 Hz, 1H), 3.60 (q, J = 6.8 Hz, 1H), 3.66 (m, 1H), 3.60 (s, 3H), 3.53 (s, 3H), 3.51 (s, 3H), 3.5-3.4 (m, 2H), 1.34 (d, J = 6.4 Hz, 3H) |
| E-38 | OCH$_3$ | OCH$_3$ | OCH$_3$ | CH$_2$OCH$_3$ | D-glucose | 251.8 (M + H)$^+$ | 82° C. | 5.6 (br s, 2H), 5.1 (d, J = 4 Hz, 1H), 3.7 (s, 3H), 3.55 (s, 3H), 3.53 (s, 3H), 3.41 (s, 3H), 3.65-3.35 (series of m, 3H), 3.4 (m, 1H), 3.2 (m, 2H) |

TABLE 4

$$Ar_1-E[G]M-Ar_2-J[L]K-O\text{-sugar}$$

Structure: pyranose ring with R1, R2, R3, R4 substituents.

| BAW 50 | BAW HTS | Compound | Ar1 | E | G | M | Ar2 | J | L | K | R1 | R2 | R3 | R4 | anomer | sugar |
|---|---|---|---|---|---|---|---|---|---|---|---|---|---|---|---|---|
| A | A | 1 | 4-CF$_3$O-C$_6$H$_4$- | CH | double | CH | 1,4-C$_6$H$_4$ | CH | double | N | OCH$_3$ | OC$_3$H$_7$ | OCH$_3$ | CH$_3$ | α | L-rhamnose |
| A | A | 2 | 4-CF$_3$-C$_6$H$_4$- | CH | double | CH | 1,4-C$_6$H$_4$ | CH | double | N | OCH$_3$ | OC$_2$H$_5$ | OCH$_3$ | CH$_3$ | α | L-rhamnose |
| B | B | 3 | 4-C$_3$F$_7$-OC$_2$F$_4$-C$_6$H$_4$- | CH | double | CH | 1,4-C$_6$H$_4$ | CH | double | N | OCH$_3$ | OC$_2$H$_5$ | OCH$_3$ | CH$_3$ | α | L-rhamnose |
| B | B | 4 | 4-CH$_3$CO-C$_6$H$_4$- | CH | double | CH | 1,4-C$_6$H$_4$ | CH | double | N | OCH$_3$ | OC$_2$H$_5$ | OCH$_3$ | CH$_3$ | α | L-rhamnose |
| A | B | 5 | 4-CF$_3$O-C$_6$H$_4$- | CH | double | CH | 1,4-C$_6$H$_4$ | CH | double | N | OCH$_3$ | OC$_2$H$_5$ | OCH$_3$ | CH$_3$ | α | L-rhamnose |
| A | A | 6 | 3-CF$_3$-C$_6$H$_4$- | CH | double | CH | 1,4-C$_6$H$_4$ | CH | double | N | OCH$_3$ | OC$_2$H$_5$ | OCH$_3$ | CH$_3$ | α | L-rhamnose |

TABLE 4-continued

Ar₁—E[G]M—Ar₂—J[L]K—O-[sugar with R1, R2, R3, R4]

| BAW 50 | BAW HTS | Compound | Ar1 | E | G | M | Ar2 | J | L | K | R1 | R2 | R3 | R4 | anomer | sugar |
|---|---|---|---|---|---|---|---|---|---|---|---|---|---|---|---|
| A | B | 7 | C₂F₅O-phenyl-E | CH | double | CH | M-phenyl-J | CH | double | N | OCH₃ | OC₂H₅ | OCH₃ | CH₃ | α | L-rhamnose |
| A | A | 8 | CF₃O-phenyl-E | CH | double | CH | M-phenyl-J | CH | double | N | OCH₃ | OCH₃ | OCH₃ | CH₃ | α | L-rhamnose |
| A | B | 9 | CF₃-phenyl-E (meta) | CH | double | CH | M-phenyl-J | CH | double | N | OCH₃ | OCH₃ | OCH₃ | CH₃ | α | L-rhamnose |
| A | A | 10 | CF₃-phenyl-E | CH | double | CH | M-phenyl-J | CH | double | N | OCH₃ | OC₃H₇ | OCH₃ | CH₃ | α | L-rhamnose |
| B | A | 11 | (CF₃)₂C(OH)-phenyl-E | CH | double | CH | M-phenyl-J | CH | double | N | OCH₃ | OC₂H₅ | OCH₃ | CH₃ | α | L-rhamnose |
| A | A | 12 | CF₃-phenyl-E | CH | double | CH | M-phenyl-J | CH | double | N | OCH₃ | OCH₃ | OCH₃ | CH₃ | α | L-rhamnose |

TABLE 4-continued $Ar_1-E[G]M-Ar_2-J[L]K-O$ (sugar structure with R1, R2, R3, R4)

| BAW 50 | BAW HTS | Compound | Ar1 | E | G | M | Ar2 | J | L | K | R1 | R2 | R3 | R4 | anomer | sugar |
|---|---|---|---|---|---|---|---|---|---|---|---|---|---|---|---|---|
| A | A | 13 | CF$_3$O–C$_6$H$_4$–E | C | triple | C | M–C$_6$H$_4$–J | CH | double | N | OCH$_3$ | OC$_2$H$_5$ | OCH$_3$ | CH$_3$ | α | L-rhamnose |
| A | A | 14 | CF$_3$–C$_6$H$_4$–E | C | triple | C | M–C$_6$H$_4$–J | CH | double | N | OCH$_3$ | OCH$_3$ | OCH$_3$ | CH$_3$ | α | L-rhamnose |
| A | A | 15 | CF$_3$–C$_6$H$_4$–E | C | triple | C | M–C$_6$H$_4$–J | CH | double | N | OCH$_3$ | OCH$_3$ | OCH$_3$ | CH$_3$ | α | L-rhamnose |
| A | A | 16 | CF$_3$–C$_6$H$_4$–E | CH | double | CH | M–C$_6$H$_4$–J | NH | single | CO | OCH$_3$ | OC$_2$H$_5$ | OCH$_3$ | CH$_3$ | α | L-rhamnose |
| A | B | 17 | C$_2$H$_5$O–C$_6$H$_4$–E | CH | double | CH | M–C$_6$H$_4$–J | NH | single | CO | OCH$_3$ | OCH3 | OCH$_3$ | CH$_3$ | α | L-rhamnose |
| A | B | 18 | C$_2$F$_5$O–C$_6$H$_4$–E | CH | double | C | M–C$_6$H$_4$–J | NH | single | CO | OCH$_3$ | OC$_3$H$_7$ | OCH$_3$ | CH$_3$ | α | L-rhamnose |
| A | A | 19 | CF$_3$O–C$_6$H$_4$–E | N | double | N | M–C$_6$H$_4$–J | N | single | CO | OCH$_3$ | OC$_2$H$_5$ | OCH$_3$ | CH$_3$ | α | L-rhamnose |

TABLE 4-continued

| BAW 50 | BAW HTS | Compound | Ar1 | E | G | Ar2 | M | J | L | K | R1 | R2 | R3 | R4 | anomer | sugar |
|---|---|---|---|---|---|---|---|---|---|---|---|---|---|---|---|---|
| A | A | 20 | CF3O–⟨⟩–E | N | double | M–⟨⟩–J | N | N | single | CO | OCH3 | OC2H5 | OCH3 | CH3 | α | L-rhamnose |
| B | A | 21 | CF3–⟨⟩–E | N | double | M–⟨⟩–J | N | N | single | CO | OCH3 | OC2H5 | OCH3 | CH3 | α | L-rhamnose |
| A | A | 22 | C2F5O–⟨⟩–E | N | double | M–⟨⟩–J | N | N | single | CO | OCH3 | OC2H5 | OCH3 | CH3 | α | L-rhamnose |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water-soluble form e.g. (2,4-dichlorophenoxy)acetic acid dimethyl amine salt is a more water-soluble form of (2,4-dichlorophenoxy)acetic acid, a well known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides.*

In another embodiment, the invention disclosed in this document can be used to control Dermaptera (earwigs).

In another embodiment, the invention disclosed in this document can be used to control Dictyoptera (cockroaches).

A non-exhaustive list of these pests includes, but is not limited to, *Blattella germanica* (German cockroach), *Blatta orientalis* (oriental cockroach), *Parcoblatta pennsylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pycnoscelus surinamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea,* and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea grandiosella* (southwestern corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinae* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angularwinged katydid), *Pterophylla* spp. (katydids), *Schistocerca gregaria, Scudderia furcata* (forktailed bush katydid), and *Valanga nigricornis*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In another embodiment, the invention disclosed in this document can be used to control Siphonaptera (fleas). A non-exhaustive list of these pests includes, but is not limited to, *Ctenocephalides canis* (dog flea), *Ctenocephalides fells* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella schultzei, Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panony-*

*chus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartwom), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "Handbook of Pest Control—The Behavior, Life History, and Control of Household Pests" by Arnold Mallis, 9th Edition, copyright 2004 by GIE Media Inc.

Mixtures

Some of the pesticides that can be employed beneficially in combination with the invention disclosed in this document include, but are not limited to the following:

1,2-dichloropropane, 1,3-dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, AKD-1022, amidithion, amidoflumet, aminocarb, amiton, amitraz, anabasine, arsenous oxide, athidathion, azadirachtin, azamethiphos, azinphos-ethyl, azinphos-methyl, azobenzene, azocyclotin, azothoate,

*Bacillus thuringiensis*, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos-ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, 3-(4-chloro-2,6-dimethylphenyl)-4-hydroxy-8-oxa-1-azaspiro[4,5]dec-3-en-2-one, 3-(4'-chloro-2,4-dimethyl[1,1'-biphenyl]-3-yl)-4-hydroxy-8-oxa-1-azaspiro[4,5]dec-3-en-2-one, 4-[[(6-chloro-3-pyridinyl)methyl]methylamino]-2(5H)-furanone, 4-[[(6-chloro-3-pyridinyl)methyl]cyclopropylamino]-2(5H)-furanone, 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A & B, crufomate, cryolite, cyanofenphos, cyanophos, cyanthoate, cyanthraniliprole, cyclethrin, cyclopro-thrin, cyenopyrafen, cyflumetofen, cyfluthrin, cyhalothrin, cyhexatin, cypermethrin, cyphenothrin, cyromazine, cythioate, 2-cyano-N-ethyl-4-fluoro-3-methoxy-benenesulfonamide, 2-cyano-N-ethyl-3-methoxy-benzenesulfonamide, 2-cyano-3-difluoromethoxy-N-ethyl-4-fluorobenzenesulfonamide, 2-cyano-3-fluoromethoxy-N-ethyl-benzenesulfonamide, 2-cyano-6-fluoro-3-methoxy-N,N-dimethylbenzenesulfonamide, 2-cyano-N-ethyl-6-fluoro-3-methoxy-N-methyl-benzenesulfonamide, 2-cyano-3-difluoromethoxy-N,N-dimethylbenzenesulfonamide, d-limonene, dazomet, DBCP, DCIP, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphone, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, 3-(difluoromethyl)-N-[2-(3,3-dimethylbutyl)phenyl]-1-methyl-1H-pyrazole-4-carboxamide, dilor, dimefluthrin, dimefox, dimetan, dimethoate, dimethrin, dimethylvinphos, dimetilan, dinex, dinobuton, dinocap, dinocap-4, dinocap-6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, emamectin benzoate, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, F1050, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion-ethyl, fentrifanil, fenvalerate, fipronil, FKI-1033, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imidaclothiz, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, JS118, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nereistoxin, N-ethyl-2,2-dimethylpropionamide-2-(2,6-dichloro-α,α,α-trifluoro-p-tolyl) hydrazone, N-ethyl-2,2-dichloro-1-methylcyclopropane-carboxamide-2-(2,6-dichloro-α,α,α-trifluoro-p-tolyl) hydrazone nicotine, nifluridide, nikkomycins, nitenpyram, nithiazine, nitrilacarb, novaluron, noviflumuron, omethoate, oxamyl, oxydemeton-methyl, oxydeprofos, oxydisulfoton, paradichlorobenzene, parathion, parathion-methyl, penfluron, pentachlorophenol, pentmethrin, permethrin, phenkapton, phenothrin, phenthoate, phorate, phosalone, phosfolan, phosmet, phosnichlor, phosphamidon, phosphine, phosphocarb, phoxim, phoxim-methyl, piperonyl butoxide, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, Qcide, quassia, quinalphos, quinalphos-methyl, quinothion, quantiofos, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfoxaflor, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetramethylfluthrin, tetranactin, tetrasul, theta-cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, verticilide XMC, xylylcarb, zeta-cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

Additionally, the following commonly know compounds can be used with this invention, luensulfone, fufenozide, pymetrozine, IKA-2002, IKI-2002, ZJ0967, IPP-10, JT-L001, N-Ethyl-2,2-dichloro-1-methylcyclopropanecarboxamide-2-(2,6-dichloro-alpha, alpha, alpha-trifluoro-p-tolyl)hydrazone.

For more information consult "Compendium of Pesticide Common Names" located at http://www.alanwood.net/pesticides/index.html as of the filing date of this document. Also consult "The Pesticide Manual" 14$^{th}$ Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of modes of action include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of Pesticide Formulation Types and International Coding System" Technical Monograph n°2, 5$^{th}$ Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which. in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE."

For further information consult "Insect Pest Management" $2^{nd}$ Edition by D. Dent, copyright CAB International (2000). Additionally, for more detailed information consult "Handbook of Pest Control—The Behavior, Life History, and Control of Household Pests" by Arnold Mallis, $9^{th}$ Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates, In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazolin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by a pest, for example, vegetable crops, fruit and nut trees, grape vines, ornamental plants, domesticated animals, the interior or exterior surfaces of buildings, and the soil around buildings.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include seeds or plants expressing proteins and/or double stranded RNA toxic to invertebrate pests, such as *Bacillus thuringiensis*, Bt Cry toxins, Bt Vip toxins, RNAi, or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis*, RNAi, or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping (which for the avoidance of doubt includes pets, for example, cats, dogs, and birds). Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

What is claimed is:

1. A compound having the following formula:

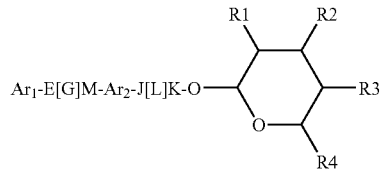

wherein:
(a) $Ar_1$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), ($C_1$-$C_6$ haloalkyl)$O(C_1$-$C_6$ haloalkyl)$O$, $C_1$-$C_6$ (hydroxy)haloalkyl, $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$$(C)_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl) phenyl, and phenoxy);
(b) E is N, C, or CR5;
(c) G is a double or triple bond;
(d) M is N, C, or CR5, (provided that when E is a nitrogen atom "N" then M is a nitrogen atom "N", and when E is a carbon atom "C", then M is a carbon atom "C", and when E is "CR5" then M is "CR5";

(c) Ar₂ is
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, NO₂, C₁-C₆ alkyl, C₁-C₆ haloalkyl, C₁-C₆ hydroxyalkyl, C₃-C₆ cycloalkyl, C₃-C₆ halocycloalkyl, C₃-C₆ hydroxycycloalkyl, C₃-C₆ cycloalkoxy, C₃-C₆ halocycloalkoxy, C₃-C₆ hydroxycycloalkoxy, C₁-C₆ alkoxy, C₁-C₆ haloalkoxy, C₂-C₆ alkenyl, C₂-C₆ alkynyl, S(=O)ₙ(C₁-C₆ alkyl), S(=O)ₙ(C₁-C₆ haloalkyl), OSO₂(C₁-C₆ alkyl), OSO₂(C₁-C₆ haloalkyl), C(=O)H, C(=O)NRₓRᵧ, (C₁-C₆ alkyl)NRₓRᵧ, C(=O)(C₁-C₆ alkyl), C(=O)O(C₁-C₆ alkyl), C(=O)(C₁-C₆ haloalkyl), C(=O)O(C₁-C₆ haloalkyl), C(=O)(C₃-C₆ cycloalkyl), C(=O)O(C₃-C₆ cycloalkyl), C(=O)(C₂-C₆ alkenyl), C(=O)O(C₂-C₆ alkenyl), (C₁-C₆ alkyl)O(C₁-C₆ alkyl), (C₁-C₆ alkyl)S(C₁-C₆ alkyl), (C₁-C₆ haloalkyl)O(C₁-C₆ haloalkyl)O, C₁-C₆ (hydroxy)(halo)alkyl, C(=O)(C₁-C₆ alkyl)C(=O)O(C₁-C₆ alkyl), phenyl, phenoxy, substituted phenyl and substituted phenoxy (wherein such substituted phenyl and substituted phenoxy have one or more substituents independently selected from H, F, Cl, Br, I, CN, NO₂, C₁-C₆ alkyl, C₁-C₆ haloalkyl, C₁-C₆ hydroxyalkyl, C₃-C₆ cycloalkyl, C₃-C₆ halocycloalkyl, C₃-C₆ hydroxycycloalkyl, C₃-C₆ cycloalkoxy, C₃-C₆ halocycloalkoxy, C₃-C₆ hydroxycycloalkoxy, C₁-C₆ alkoxy, C₁-C₆ haloalkoxy, C₂-C₆ alkenyl, C₂-C₆ alkynyl, S(=O)ₙ(C₁-C₆ alkyl), S(=O)ₙ(C₁-C₆ haloalkyl), OSO₂(C₁-C₆ alkyl), OSO₂(C₁-C₆ haloalkyl), C(=O)H, C(=O)NRₓRᵧ, (C₁-C₆ alkyl)NRₓRᵧ, C(=O)(C₁-C₆ alkyl), C(=O)O(C₁-C₆ alkyl), C(=O)(C₁-C₆ haloalkyl), C(=O)O(C₁-C₆ haloalkyl), C(=O)(C₃-C₆ cycloalkyl), C(=O)O(C₃-C₆ cycloalkyl), C(=O)(C₂-C₆ alkenyl), C(=O)O(C₂-C₆ alkenyl), (C₁-C₆ alkyl)O(C₁-C₆ alkyl), (C₁-C₆ alkyl)S(C₁-C₆ alkyl), C(=O)(C₁-C₆ alkyl)C(=O)O(C₁-C₆ alkyl) phenyl, and phenoxy);
(d) J is O, N, NR5, CR5, or C=O;
(e) L is a single or double bond;
(f) K is CR5, C=O, N, NR5, or C=S;
(g) R1 is H, OH, F, Cl, Br, I, oxo, C₁-C₆ alkyl, C₁-C₆ haloalkyl, C₁-C₆ alkoxy, C₃-C₆ cycloalkoxy, C₁-C₆ haloalkoxy, C₂-C₆ alkenyloxy, (C₁-C₆ alkyl)O(C₁-C₆ alkyl), (C₁-C₆ alkyl)O(C₁-C₆ alkoxy), OC(=O)(C₁-C₆ alkyl), OC(=O)(C₃-C₆ cycloalkyl), OC(=O)(C₁-C₆ haloalkyl), OC(=O)(C₂-C₆ alkenyl), or NRₓRᵧ;
(h) R2 is H, F, Cl, Br, I, oxo, C₁-C₆ alkyl, C₁-C₆ haloalkyl, C₁-C₆ alkoxy, C₃-C₆ cycloalkoxy, C₁-C₆ haloalkoxy, C₂-C₆ alkenyloxy, (C₁-C₆ alkyl)O(C₁-C₆ alkyl), (C₁-C₆ alkyl)O(C₁-C₆ alkoxy), OC(=O)(C₁-C₆ alkyl), OC(=O)(C₃-C₆ cycloalkyl), OC(=O)(C₁-C₆ haloalkyl), OC(=O)(C₂-C₆ alkenyl), or NRₓRᵧ;
(i) R3 is H, OH, F, Cl, Br, I, oxo, C₁-C₆ alkyl, C₁-C₆ haloalkyl, C₁-C₆ alkoxy, C₃-C₆ cycloalkoxy, C₁-C₆ haloalkoxy, C₂-C₆ alkenyloxy, (C₁-C₆ alkyl)O(C₁-C₆ alkyl), (C₁-C₆ alkyl)O(C₁-C₆ alkoxy), OC(=O)(C₁-C₆ alkyl), OC(=O)(C₃-C₆ cycloalkyl), OC(=O)(C₁-C₆ haloalkyl), OC(=O)(C₂-C₆ alkenyl), or NRₓRᵧ;
(j) R4 is H, C₁-C₆ alkyl, C₁-C₆ haloalkyl, C₁-C₆ alkoxy, C₁-C₆ haloalkoxy, C₂-C₆ alkenyloxy, (C₁-C₆ alkyl)O(C₁-C₆ alkyl);
(k) R5 is (each independently) H, C₁-C₆ alkyl, C₁-C₆ haloalkyl, C₃-C₆ cycloalkyl, or C₃-C₆ halocycloalkyl; and
(l) Rₓ and Rᵧ are independently selected from H, C₁-C₆ alkyl, C₁-C₆ haloalkyl, C₁-C₆ hydroxyalkyl, C₃-C₆ cycloalkyl, C₃-C₆ halocycloalkyl, C₃-C₆ hydroxycycloalkyl, C₃-C₆ cycloalkoxy, C₃-C₆ halocycloalkoxy, C₃-C₆ hydroxycycloalkoxy, C₁-C₆ alkoxy, C₁-C₆ haloalkoxy, C₂-C₆ alkenyl, C₂-C₆ alkynyl, S(=O)ₙ(C₁-C₆ alkyl), S(=O)ₙ(C₁-C₆ haloalkyl), OSO₂(C₁-C₆ alkyl), OSO₂(C₁-C₆ haloalkyl), C(=O)H, C(=O)OH, C(=O)(C₁-C₆ alkyl), C(=O)O(C₁-C₆ alkyl), C(=O)(C₁-C₆ haloalkyl), C(=O)O(C₁-C₆ haloalkyl), C(=O)(C₃-C₆ cycloalkyl), C(=O)O(C₃-C₆ cycloalkyl), C(=O)(C₂-C₆ alkenyl), C(=O)O(C₂-C₆ alkenyl), (C₁-C₆ alkyl)O(C₁-C₆ alkyl), (C₁-C₆ alkyl)S(C₁-C₆ alkyl), C(=O)(C₁-C₆ alkyl)C(=O)O(C₁-C₆ alkyl), phenyl, and phenoxy.

2. A compound according to claim 1 having one of the following structures

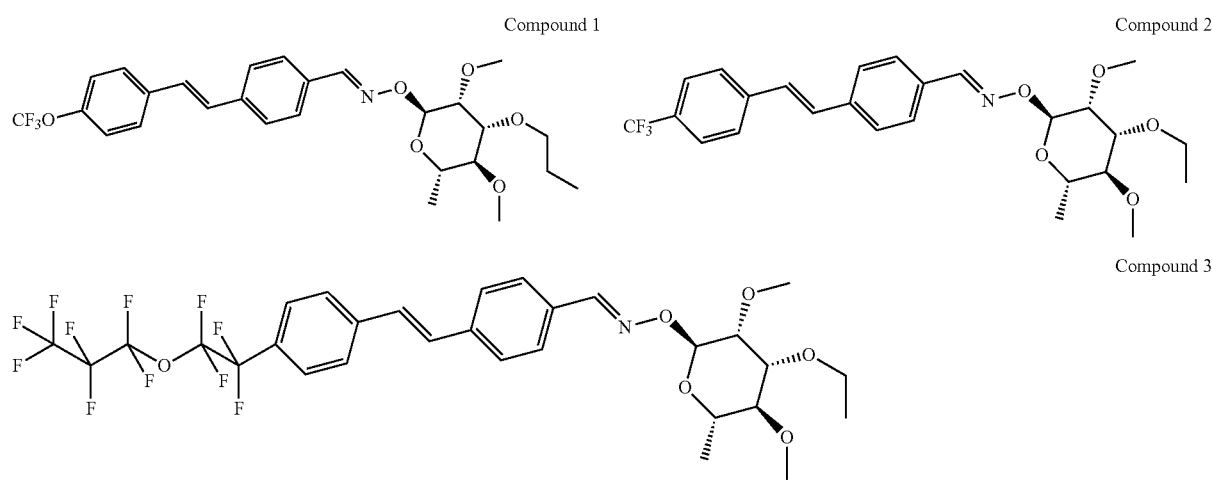

Compound 1

Compound 2

Compound 3

-continued
Compound 4
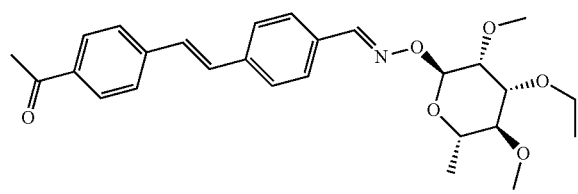
Compound 5
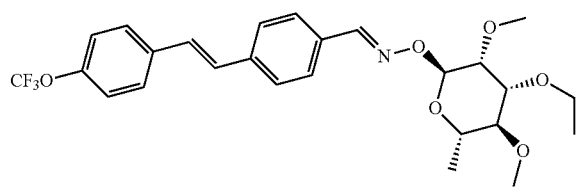
Compound 6
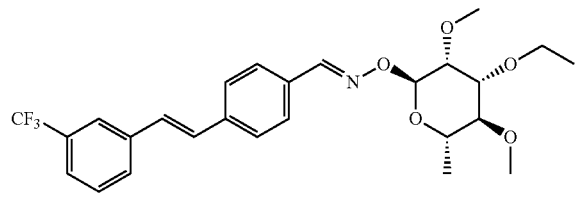
Compound 7
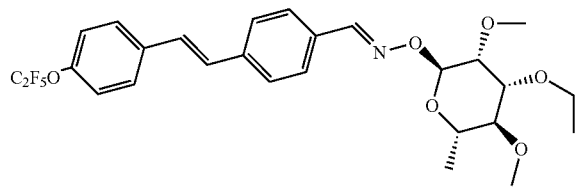
Compound 8
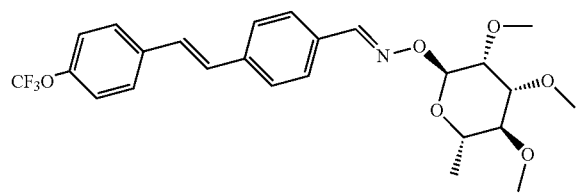
Compound 9
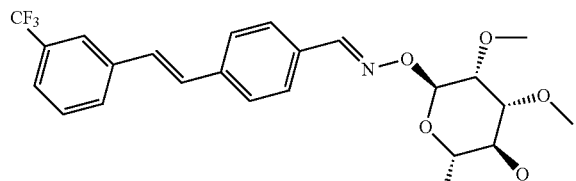
Compound 10
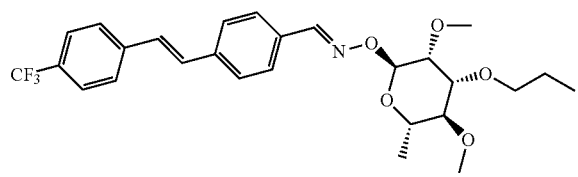
Compound 11
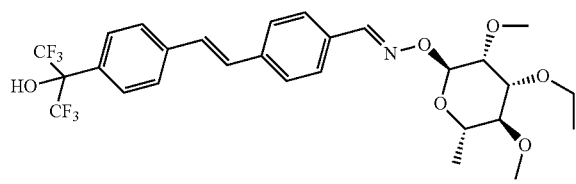
Compound 12
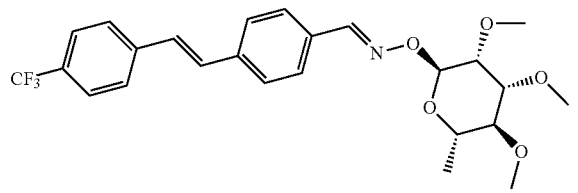
Compound 13
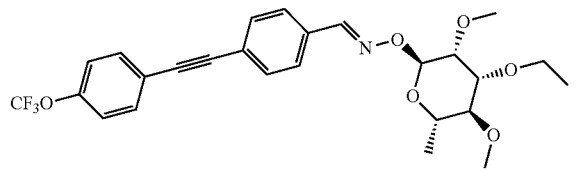
Compound 14
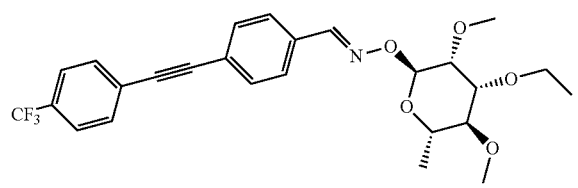
Compound 15
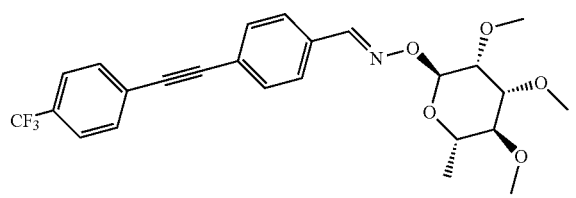
Compound 16
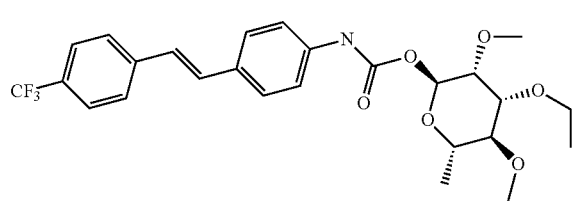
Compound 17
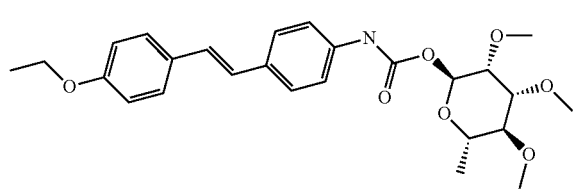

-continued

Compound 18

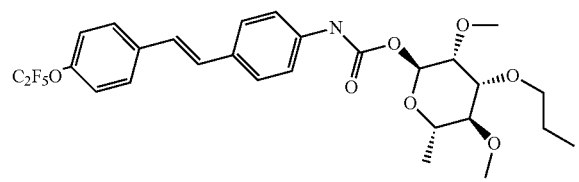

Compound 19

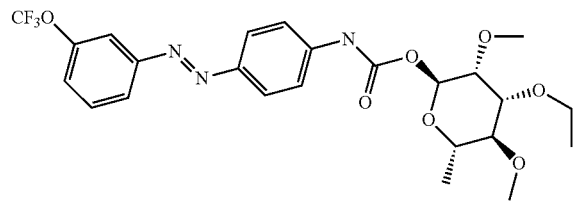

Compound 20

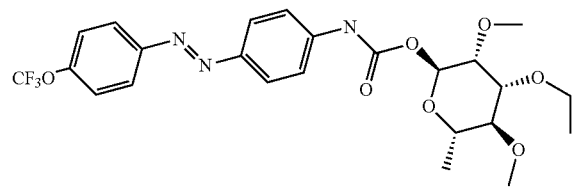

Compound 21

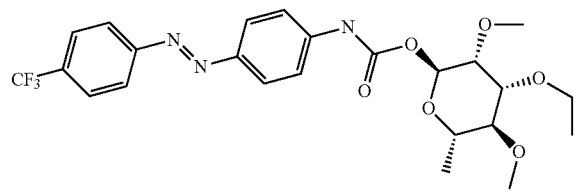

Compound 22

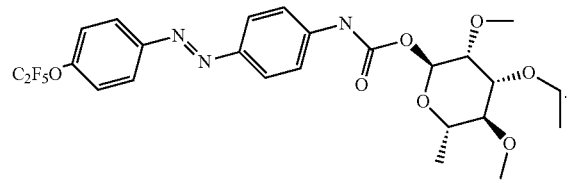

3. A compound that is a pesticidally acceptable acid addition salt of a compound according to claim 2.

4. A process comprising applying a compound according to claim 1 to a locus to control pests.

5. A composition comprising a mixture of a compound according to claim 2 with at least one other pesticide.

6. A process of applying a compound according to claim 1 to a seed.

7. A process of orally administering or applying a compound of claim 1 to an animal.

* * * * *